(12) United States Patent
Jak et al.

(10) Patent No.: US 10,379,445 B2
(45) Date of Patent: *Aug. 13, 2019

(54) METROLOGY METHOD, TARGET AND SUBSTRATE

(71) Applicant: ASML NETHERLANDS B.V., Veldhoven (NL)

(72) Inventors: Martin Jacobus Johan Jak, s-Hertogenbosch (NL); Arie Jeffrey Den Boef, Waalre (NL); Martin Ebert, Valkenswaard (NL)

(73) Assignee: ASML Netherlands B.V., Veldhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/174,398

(22) Filed: Oct. 30, 2018

(65) Prior Publication Data

US 2019/0064677 A1 Feb. 28, 2019

Related U.S. Application Data

(63) Continuation of application No. 15/387,431, filed on Dec. 21, 2016, now Pat. No. 10,133,188.

(30) Foreign Application Priority Data

Dec. 23, 2015 (EP) ..................... 15202372

(51) Int. Cl.
*G03B 27/54* (2006.01)
*G03F 7/20* (2006.01)
(Continued)

(52) U.S. Cl.
CPC .......... *G03F 7/70191* (2013.01); *G01B 11/26* (2013.01); *G01N 21/21* (2013.01);
(Continued)

(58) Field of Classification Search
CPC . G02B 5/1819; G02B 5/1823; G03F 7/70191; G03F 7/70616; G03F 7/70633;
(Continued)

(56) References Cited

U.S. PATENT DOCUMENTS 4,577,968 A 3/1986 Makosch
5,625,453 A 4/1997 Matsumoto
(Continued)

FOREIGN PATENT DOCUMENTS

CN 101903832 12/2010
EP 0 449 582 10/1991
(Continued)

OTHER PUBLICATIONS

Yi-sha Ku et al., "Infrared differential interference contrast microscopy for 3D interconnect overlay metrology," Optics Express, vol. 21, No. 16, pp. 18884-18898 (Aug. 12, 2013).
(Continued)

*Primary Examiner* — Peter B Kim
(74) *Attorney, Agent, or Firm* — Pillsbury Winthrop Shaw Pittman LLP

(57) ABSTRACT

A method, involving illuminating at least a first periodic structure of a metrology target with a first radiation beam having a first polarization, illuminating at least a second periodic structure of the metrology target with a second radiation beam having a second different polarization, combining radiation diffracted from the first periodic structure with radiation diffracted from the second periodic structure to cause interference, detecting the combined radiation using a detector, and determining a parameter of interest from the detected combined radiation.

20 Claims, 13 Drawing Sheets

(51) Int. Cl.
  *G01B 11/26* (2006.01)
  *G01N 21/95* (2006.01)
  *G01N 21/21* (2006.01)
  *G01N 21/47* (2006.01)
  *G02B 5/18* (2006.01)
  *G03F 9/00* (2006.01)
  *G02B 27/42* (2006.01)

(52) U.S. Cl.
  CPC ..... *G01N 21/4788* (2013.01); *G01N 21/9501* (2013.01); *G02B 5/1819* (2013.01); *G02B 5/1823* (2013.01); *G02B 27/4255* (2013.01); *G02B 27/4272* (2013.01); *G03F 7/7085* (2013.01); *G03F 7/70616* (2013.01); *G03F 7/70633* (2013.01); *G03F 7/70683* (2013.01); *G03F 9/7049* (2013.01); *G03F 9/7076* (2013.01)

(58) Field of Classification Search
  CPC .. G03F 7/70683; G03F 7/7085; G03F 9/7049; G03F 9/7076; G01B 11/26
  See application file for complete search history.

(56) References Cited

U.S. PATENT DOCUMENTS

| | | | |
|---|---|---|---|
| 5,798,829 | A | 8/1998 | Vaez-Iravani |
| 6,710,876 | B1 | 3/2004 | Nikoonahad et al. |
| 7,298,481 | B2 | 11/2007 | Mieher et al. |
| 7,453,577 | B2 | 11/2008 | Van Der Werf et al. |
| 7,587,704 | B2 | 9/2009 | Ye et al. |
| 8,339,595 | B2 | 12/2012 | Den Boef |
| 8,411,287 | B2 | 4/2013 | Smilde et al. |
| 8,867,020 | B2 | 10/2014 | Smilde et al. |
| 9,081,303 | B2 | 7/2015 | Cramer et al. |
| 9,110,385 | B2 | 8/2015 | Den Boef |
| 10,133,188 | B2 * | 11/2018 | Jak ................... G03F 7/70191 |
| 2005/0088188 | A1 | 4/2005 | Borden et al. |
| 2006/0126074 | A1 | 6/2006 | Van Der Werf et al. |
| 2009/0290217 | A1 | 11/2009 | Hoose |
| 2010/0328655 | A1 | 12/2010 | Den Boef |
| 2011/0027704 | A1 | 2/2011 | Cramer et al. |
| 2011/0043791 | A1 | 2/2011 | Smilde et al. |
| 2011/0069292 | A1 | 3/2011 | Den Boef |
| 2012/0242970 | A1 | 9/2012 | Smilde et al. |
| 2014/0118721 | A1 | 5/2014 | Shyu et al. |
| 2015/0204664 | A1 | 7/2015 | Bringoltz et al. |
| 2016/0161863 | A1 | 6/2016 | Den Boef et al. |
| 2016/0313654 | A1 | 10/2016 | Zeng et al. |
| 2016/0370717 | A1 | 12/2016 | Den Boef et al. |

FOREIGN PATENT DOCUMENTS

| | | |
|---|---|---|
| EP | 0534759 | 3/1993 |
| JP | S5750611 | 3/1982 |
| JP | H0590126 | 4/1993 |
| JP | 2006170996 | 6/2006 |
| WO | 2009/078708 | 6/2009 |
| WO | 2009/106279 | 9/2009 |
| WO | 2011/012624 | 2/2011 |

OTHER PUBLICATIONS

Yi-sha Ku et al., "Infrared Differential Interference Contrast Microscopy for Overlay Metrology on 3D-Interconnect bonded Wafers," Proc. of SPIE, vol. 8788, pp. 87881Z-1-87881Z-8 (May 13, 2013).

International Search Report and Written Opinion dated Mar. 9, 2017 in corresponding International Patent Application No. PCT/EP2016/080137.

Taiwan Office Action dated Nov. 10, 2017 in corresponding Taiwan Patent Application No. 105142816.

Japanese Office Action issued in corresponding Japanese Patent Application No. 2018-532375, dated Jun. 25, 2019.

* cited by examiner

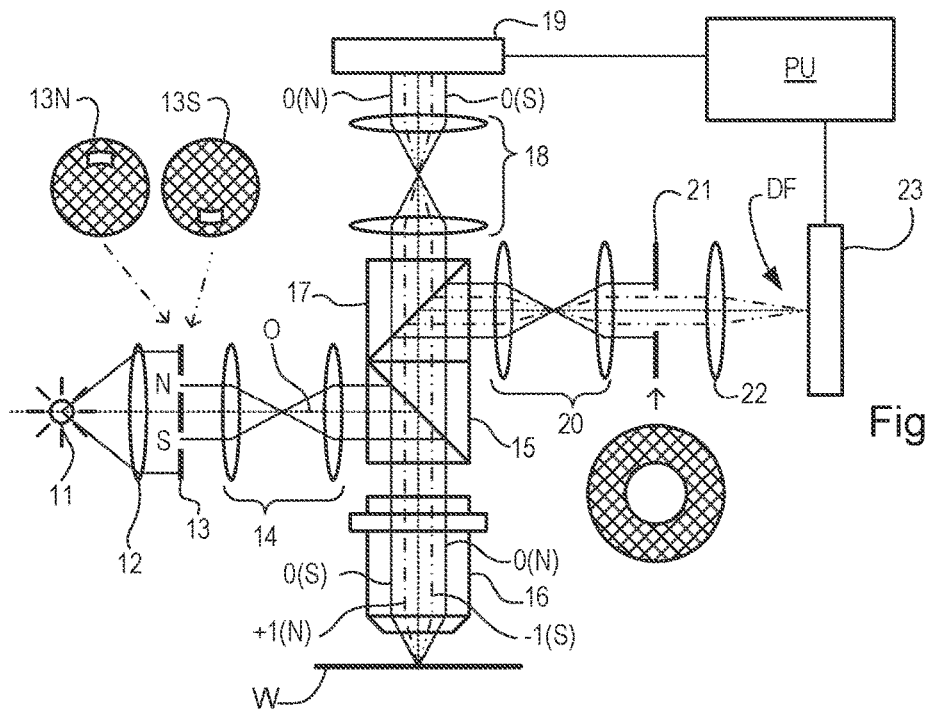
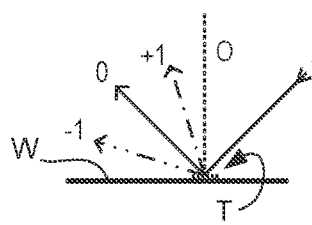
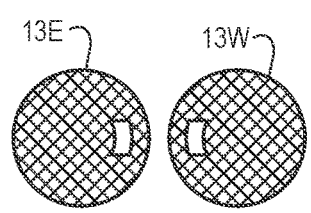
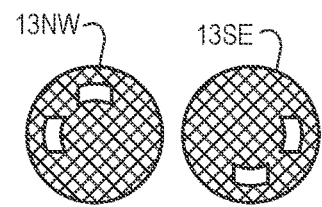
Fig. 3(b)　　　Fig. 3(c)　　　Fig. 3(d)
(PRIOR ART)
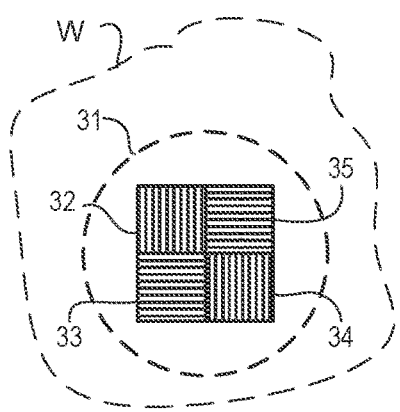
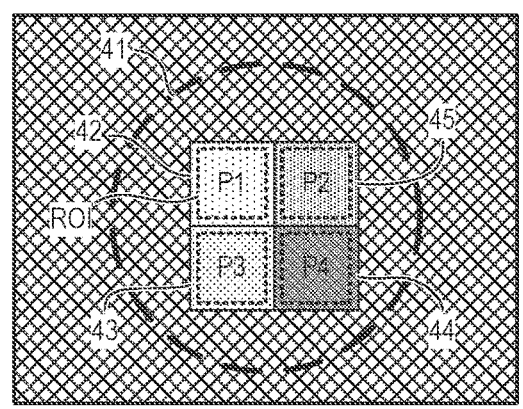
Fig. 4 (PRIOR ART)　　　Fig. 5 (PRIOR ART)

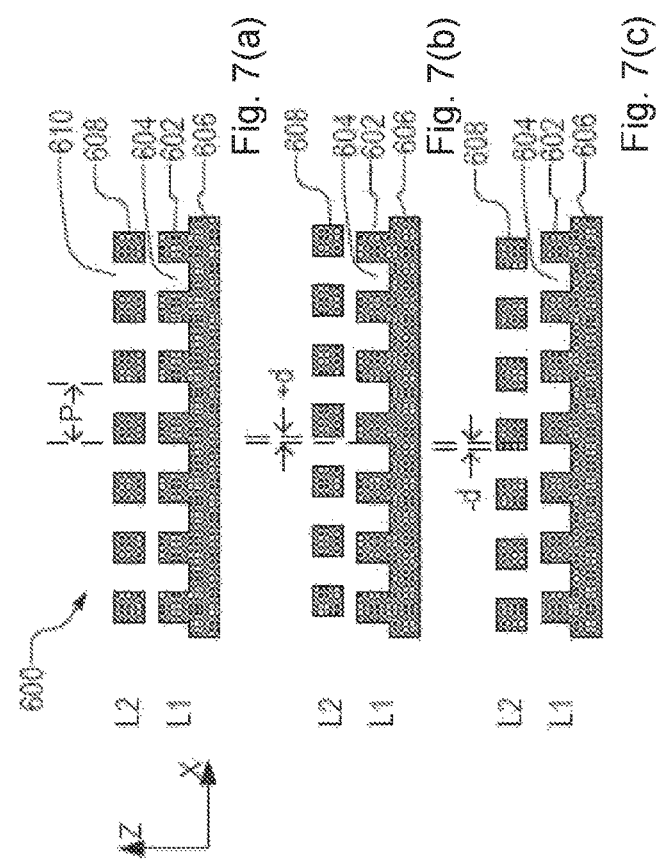
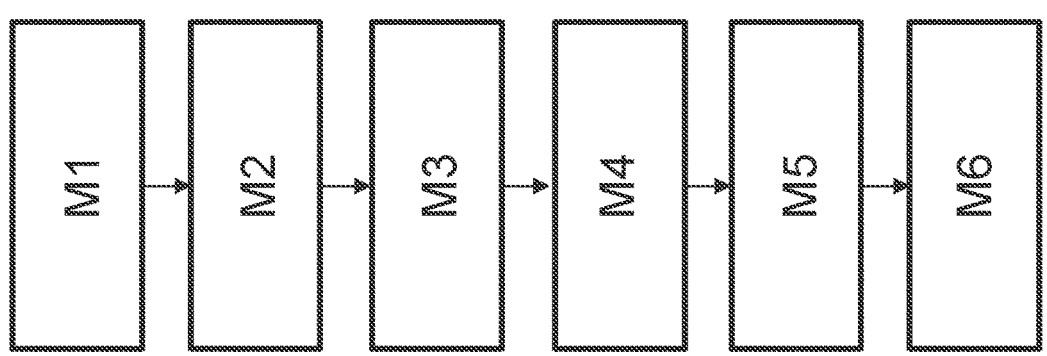
Fig. 6

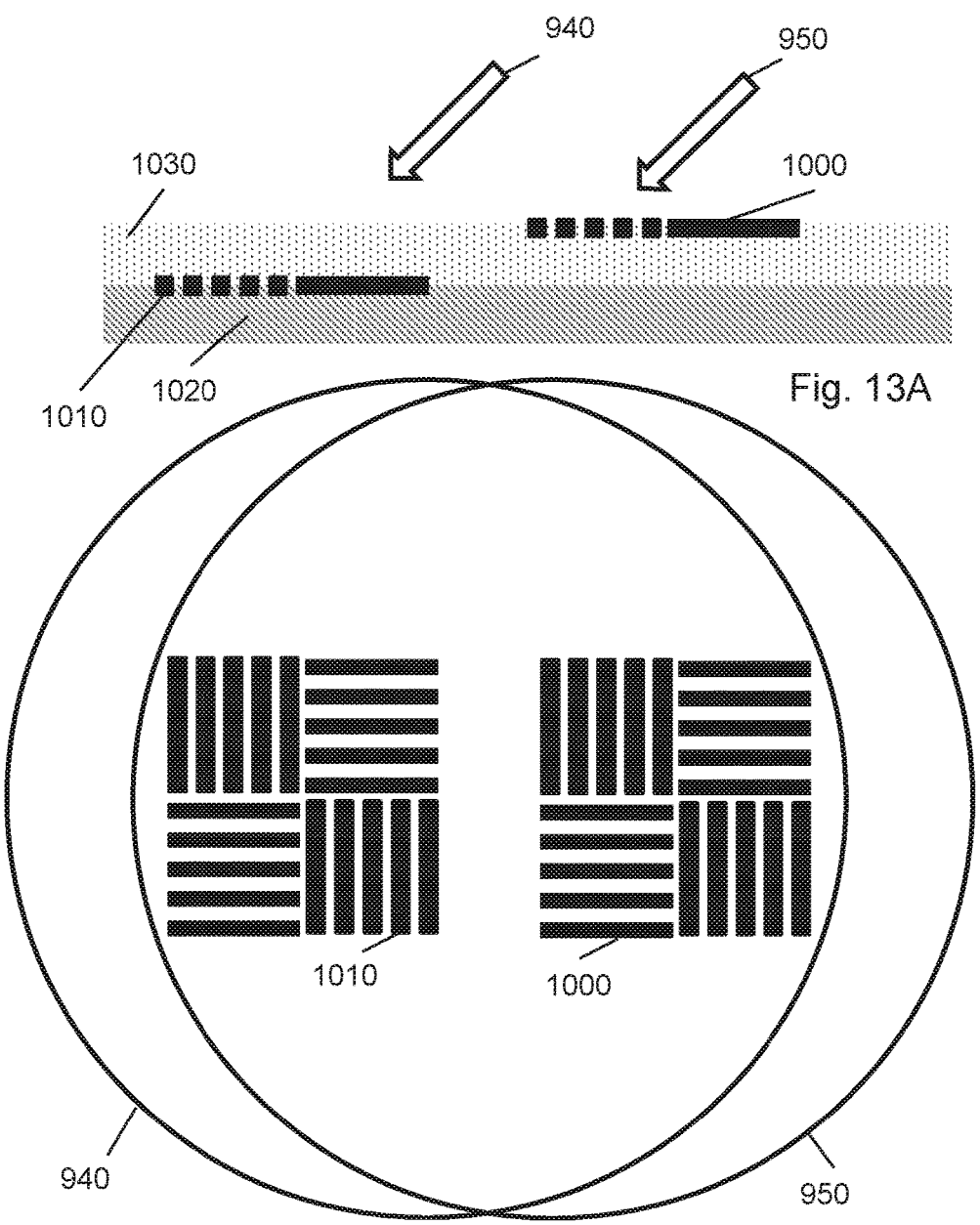

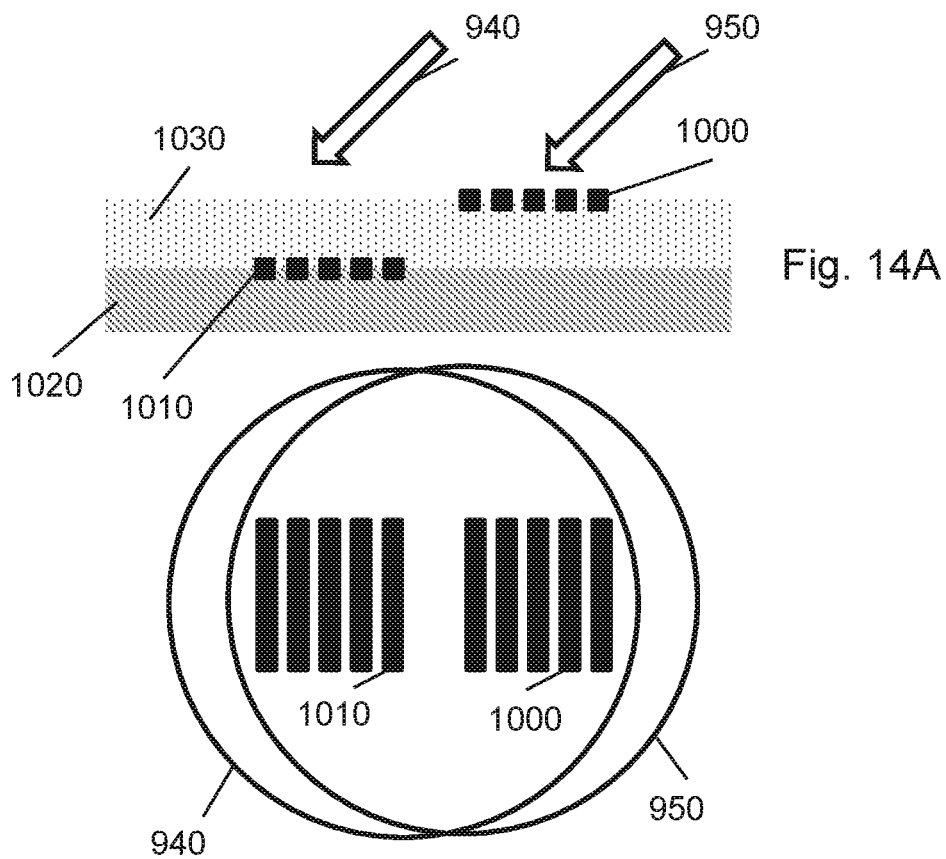
Fig. 14A
Fig. 14B
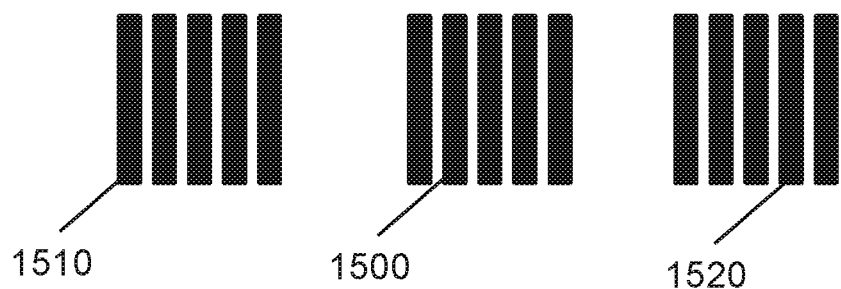
Fig. 15

METROLOGY METHOD, TARGET AND SUBSTRATE

The present application is a continuation of U.S. patent application Ser. No. 15/387,431, filed on Dec. 21, 2016, which claims the benefit of priority to European patent application no. 15202372.7, filed on Dec. 23, 2015, each of which is incorporated herein in its entirety by reference.

FIELD

The present description relates to a method, apparatus, and substrate for metrology usable, for example, in the manufacture of devices by a patterning process and to a method of manufacturing devices using a patterning process.

BACKGROUND

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., comprising part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned. Known lithographic apparatus include so-called steppers, in which each target portion is irradiated by exposing an entire pattern onto the target portion at one time, and so-called scanners, in which each target portion is irradiated by scanning the pattern through a radiation beam in a given direction (the "scanning"-direction) while synchronously scanning the substrate parallel or anti parallel to this direction. It is also possible to transfer the pattern from the patterning device to the substrate by imprinting the pattern onto the substrate.

In a patterning process (i.e., a process of creating a device or other structure involving patterning (such as lithographic exposure or imprint), which may typically include one or more associated processing steps such as development of resist, etching, etc.), it is desirable frequently to make measurements of structures created, e.g., for process control and verification. So, in order to monitor the patterning process, one or more parameters of the patterned substrate are measured. Parameters may include, for example, the overlay error between successive layers formed in or on the patterned substrate and/or critical linewidth of developed photosensitive resist, etched structures, etc. This measurement may be performed on a target surface of a product substrate and/or in the form of a dedicated metrology target. Metrology targets (or marks) may comprise a periodic structure, for example, combinations of horizontal and vertical bars, such as gratings.

Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a "spectrum" from which a property of interest of the target can be determined. Determination of the property of interest may be performed by various techniques: e.g., reconstruction of the target structure by iterative approaches such as rigorous coupled wave analysis or finite element methods; library searches; and/or principal component analysis.

SUMMARY

It is desirable to provide a method and apparatus for metrology using a target, in which throughput, flexibility and/or accuracy can be improved. Furthermore, although not limited to this, it would be of great advantage, if this could be applied to small target structures that can be read out with a dark-field image-based technique.

In an embodiment, there is provided a method, comprising: illuminating at least a first periodic structure of a metrology target with a first radiation beam having a first polarization; illuminating at least a second periodic structure of the metrology target with a second radiation beam having a second different polarization; combining radiation diffracted from the first periodic structure with radiation diffracted from the second periodic structure to cause interference; detecting the combined radiation using a detector; and determining a parameter of interest from the detected combined radiation.

In an embodiment, there is provided a metrology apparatus comprising: an optical element configured to provide a first radiation beam having a first polarization and a second radiation beam having a second polarization onto a metrology target having a plurality of periodic structures; a detector configured to detect radiation from the first and second radiation beams diffracted by the periodic structures, wherein the diffracted radiation from the periodic structures is combined and interferes; and a control system configured to determine a parameter of interest from the detected combined diffracted radiation.

In an embodiment, there is provided a method of manufacturing devices wherein a device pattern is applied to a series of substrates using a patterning process, the method including inspecting at least a diffraction measurement target formed as part of or beside the device pattern on at least one of the substrates using a method as described herein and controlling the patterning process for later substrates in accordance with the result of the method.

In an embodiment, there is provided a non-transitory computer program product comprising machine-readable instructions for causing a processor to cause performance of a method as described herein.

In an embodiment, there is provided a non-transitory computer program product comprising machine-readable instructions for causing a processor to cause performance of a method as described herein.

In an embodiment, there is provided a system comprising: an inspection apparatus configured to provide a beam on a diffraction measurement target on a substrate and to detect radiation diffracted by the target to determine a parameter of a patterning process; and a non-transitory computer program product as described herein.

Features and/or advantages of embodiments, as well as the structure and operation of various embodiments, are described in detail herein with reference to the accompanying drawings. It is noted that the invention is not limited to the specific embodiments described herein. The embodiments are presented herein for illustrative purposes only. Additional embodiments will be apparent to persons skilled in the relevant art(s) based on the teachings contained herein.

BRIEF DESCRIPTION OF THE DRAWINGS

Embodiments will now be described, by way of example only, with reference to the accompanying drawings in which.

FIG. 3(a) is schematic diagram of an embodiment of a measurement apparatus for use in measuring targets using a first pair of illumination apertures providing certain illumination modes;

FIG. 3(b) is a schematic detail of a diffraction spectrum of a target periodic structure for a given direction of illumination;

FIG. 3(c) is a schematic illustration of a second pair of illumination apertures providing further illumination modes in using a scatterometer for diffraction based overlay measurements;

FIG. 3(d) is a schematic illustration of a third pair of illumination apertures combining the first and second pairs of apertures providing further illumination modes in using a scatterometer for diffraction based overlay measurements;

FIG. 4 depicts a form of multiple periodic structure (e.g., grating) target and an outline of a measurement spot on a substrate;

FIG. 5 depicts an image of the target of FIG. 4 obtained in the apparatus of FIG. 3;

FIG. 6 is a flowchart showing the steps of an overlay measurement method using the apparatus of FIG. 3;

FIGS. 7(a) to 7(c) show schematic cross-sections of overlay periodic structures having different overlay values in the region of zero;

FIG. 13A schematically depicts a side view of an embodiment of a metrology target in the layers of a substrate and incident measurement radiation beams;

FIG. 13B schematically depicts a top view of the metrology target and incident radiation beams of FIG. 13A;

FIG. 14A schematically depicts a side view of an embodiment of a metrology target in the layers of a substrate and incident measurement radiation beams;

FIG. 14B schematically depicts a top view of the metrology target and incident radiation beams of FIG. 14A;

FIG. 15 schematically depicts a measurement of the diffracted radiation from the target of FIG. 14;

DETAILED DESCRIPTION

Before describing embodiments in detail, it is instructive to present an example environment in which embodiments may be implemented.

Figure 1:
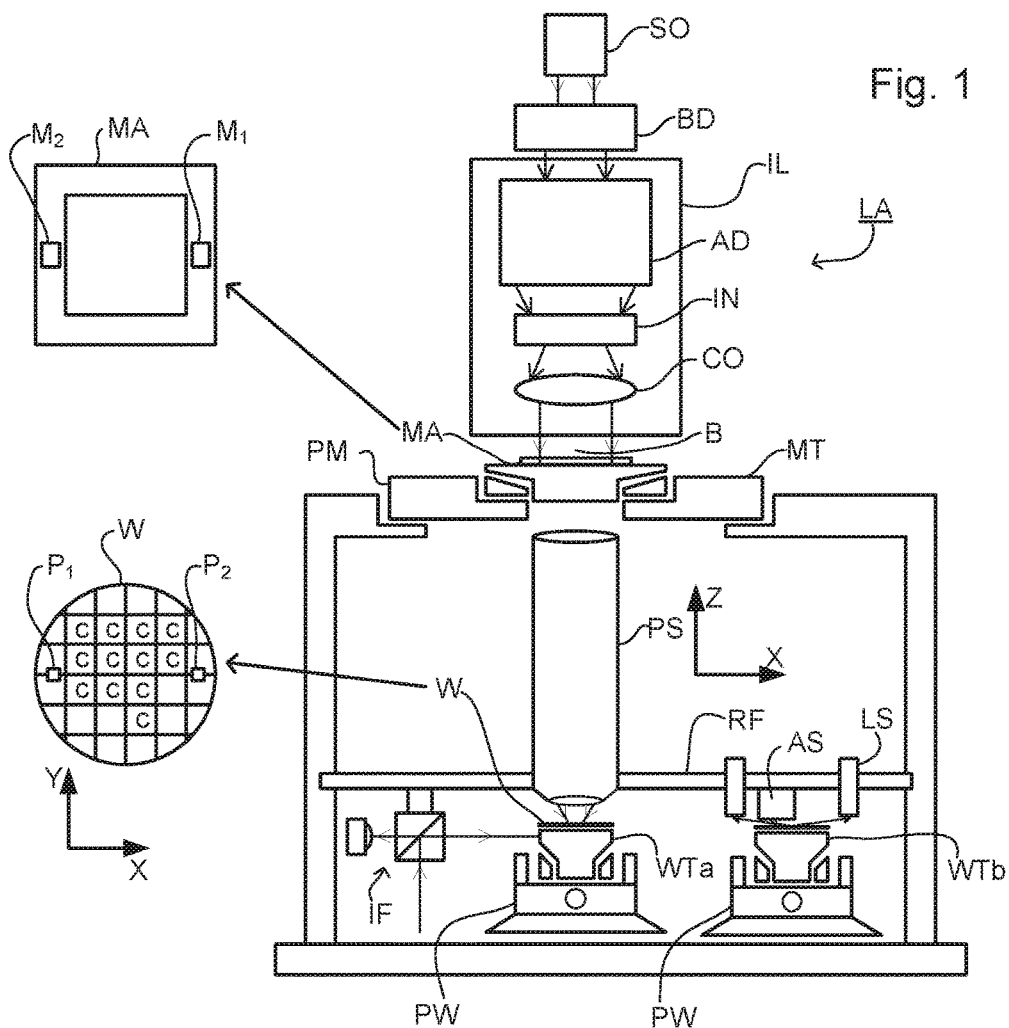
FIG. 1 depicts an embodiment of a lithographic apparatus.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; a substrate table (e.g., a wafer table) WT constructed to hold a substrate (e.g., a resist coated wafer) W and connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can use mechanical, vacuum, electrostatic or other clamping techniques to hold the patterning device. The patterning device support may be a frame or a table, for example, which may be fixed or movable as required. The patterning device support may ensure that the patterning device is at a desired position, for example with respect to the projection system. Any use of the terms "reticle" or "mask" herein may be considered synonymous with the more general term "patterning device."

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

The patterning device may be transmissive or reflective. Examples of patterning devices include masks, programmable mirror arrays, and programmable LCD panels. Masks are well known in lithography, and include mask types such as binary, alternating phase-shift, and attenuated phase-shift, as well as various hybrid mask types. An example of a programmable mirror array employs a matrix arrangement of small mirrors, each of which can be individually tilted so as to reflect an incoming radiation beam in different directions. The tilted mirrors impart a pattern in a radiation beam, which is reflected by the mirror matrix.

As here depicted, the apparatus is of a transmissive type (e.g., employing a transmissive mask). Alternatively, the apparatus may be of a reflective type (e.g., employing a programmable mirror array of a type as referred to above, or employing a reflective mask).

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems. The term "immersion" as used herein does not mean that a structure, such as a substrate, must be submerged in liquid, but rather only means that liquid is located between the projection system and the substrate during exposure.

Referring to FIG. 1, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may include an adjuster AD for adjusting the angular intensity distribution of the radiation beam. Generally, at least the outer and/or inner radial extent (commonly referred to as σ-outer and σ-inner, respectively) of the intensity distribution in a pupil plane of the illuminator can be adjusted. In addition, the illuminator IL may include various other components, such as an integrator IN and a condenser CO. The illuminator may be used to condition the radiation beam, to have a desired uniformity and intensity distribution in its cross section.

The radiation beam B is incident on the patterning device (e.g., mask) MA, which is held on the patterning device support (e.g., mask table MT), and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WT can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks $M_1$, $M_2$ and substrate alignment marks $P_1$, $P_2$. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment markers may also be included within dies, in amongst the device features, in which case it is desirable that the markers be as small as possible and not require any different imaging or process conditions than adjacent features. An embodiment of an alignment system, which can detect the alignment markers, is described further below.

The depicted apparatus could be used in at least one of the following modes:

1. In step mode, the patterning device support (e.g., mask table) MT and the substrate table WTa are kept essentially stationary, while an entire pattern imparted to the radiation beam is projected onto a target portion C at one time (i.e., a single static exposure). The substrate table WTa is then shifted in the X and/or Y direction so that a different target portion C can be exposed. In step mode, the maximum size of the exposure field limits the size of the target portion C imaged in a single static exposure.

2. In scan mode, the patterning device support (e.g., mask table) MT and the substrate table WTa are scanned synchronously while a pattern imparted to the radiation beam is projected onto a target portion C (i.e., a single dynamic exposure). The velocity and direction of the substrate table WTa relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion.

3. In another mode, the patterning device support (e.g., mask table) MT is kept essentially stationary holding a programmable patterning device, and the substrate table WTa is moved or scanned while a pattern imparted to the radiation beam is projected onto a target portion C. In this mode, generally a pulsed radiation source is employed and the programmable patterning device is updated as required after each movement of the substrate table WTa or in between successive radiation pulses during a scan. This mode of operation can be readily applied to maskless lithography that utilizes programmable patterning device, such as a programmable mirror array of a type as referred to above.

Combinations and/or variations on the above described modes of use or entirely different modes of use may also be employed.

Lithographic apparatus LA is of a so-called dual stage type which has at least two tables WTa, WTb (e.g., two substrate tables) and at least two stations—an exposure station and a measurement station—between which at least one of the tables can be exchanged. For example, while a substrate on one table is being exposed at the exposure station, another substrate can be loaded onto the other substrate table at the measurement station and various preparatory steps carried out. The preparatory steps may include mapping the surface control of the substrate using a level sensor LS and measuring the position of alignment markers on the substrate using an alignment sensor AS, both sensors being supported by a reference frame RF. If the position sensor IF is not capable of measuring the position of a table while it is at the measurement station as well as at the exposure station, a second position sensor may be provided to enable the positions of the table to be tracked at both stations. As another example, while a substrate on one table is being exposed at the exposure station, another table without a substrate waits at the measurement station (where optionally measurement activity may occur). This other table has one or more measurement devices and may optionally have other tools (e.g., cleaning apparatus). When the substrate has completed exposure, the table without a substrate moves to the exposure station to perform, e.g., measurements and the table with the substrate moves to a location (e.g., the measurement station) where the substrate is unloaded and another substrate is load. These multi-table arrangements enable a substantial increase in the throughput of the apparatus.

Figure 2:
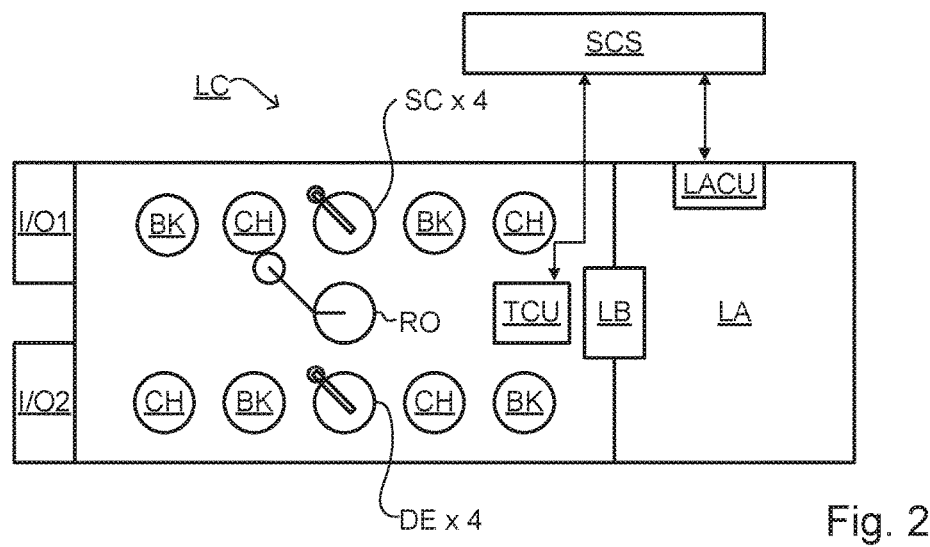
FIG. 2 depicts an embodiment of a lithographic cell or cluster.

As shown in FIG. 2, the lithographic apparatus LA forms part of a lithographic cell LC, also sometimes referred to as a lithocell or lithocluster, which also includes apparatus to perform one or more pre- and post-exposure processes on a substrate. Conventionally these include one or more spin coaters SC to deposit a resist layer, one or more developers DE to develop exposed resist, one or more chill plates CH and one or more bake plates BK. A substrate handler, or robot, RO picks up a substrate from input/output ports I/O1, I/O2, moves it between the different process devices and delivers it to the loading bay LB of the lithographic apparatus. These devices, which are often collectively referred to as the track, are under the control of a track control unit TCU which is itself controlled by the supervisory control system SCS, which also controls the lithographic apparatus via lithographic control unit LACU. Thus, the different apparatus may be operated to maximize throughput and processing efficiency.

In order that the substrate that is exposed by the lithographic apparatus is exposed correctly and consistently, it is desirable to inspect an exposed substrate to measure one or more properties such as overlay error between subsequent layers, line thickness, critical dimension (CD), etc. If an error is detected, an adjustment may be made to an exposure of one or more subsequent substrates, especially if the inspection can be done soon and fast enough that another substrate of the same lot/batch is still to be exposed. Also, an already exposed substrate may be stripped and reworked (to improve yield) or discarded, thereby avoiding performing an exposure on a substrate that is known to be faulty. In a case where only some target portions of a substrate are faulty, a further exposure may be performed only on those target portions which are good. Another possibility is to adapt a setting of a subsequent process step to compensate for the error, e.g. the time of a trim etch step can be adjusted to compensate for substrate-to-substrate CD variation resulting from the lithographic process step.

An inspection apparatus is used to determine one or more properties of a substrate, and in particular, how one or more properties of different substrates or different layers of the same substrate vary from layer to layer and/or across a substrate. The inspection apparatus may be integrated into the lithographic apparatus LA or the lithocell LC or may be a stand-alone device. To enable most rapid measurements, it is desirable that the inspection apparatus measures one or more properties in the exposed resist layer immediately after the exposure. However, the latent image in the resist has a very low contrast—there is only a very small difference in refractive index between the part of the resist which has been exposed to radiation and that which has not—and not all inspection apparatus have sufficient sensitivity to make useful measurements of the latent image. Therefore measurements may be taken after the post-exposure bake step (PEB) which is customarily the first step carried out on an exposed substrate and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibility for rework of a faulty substrate but may still provide useful information, e.g. for the purpose of process control.

A target used by a conventional scatterometer comprises a relatively large periodic structure (e.g., grating) layout, e.g., 40 μm by 40 μm. In that case, the measurement beam often has a spot size that is smaller than the periodic structure layout (i.e., the periodic structure layout is underfilled). This simplifies mathematical reconstruction of the target as it can be regarded as infinite. However, for example, so the target can be positioned in among product features, rather than in the scribe lane, the size of a target has been reduced, e.g., to 20 μm by 20 μm or less, or to 10 μm by 10 μm or less. In this situation, the periodic structure layout may be made smaller than the measurement spot (i.e., the periodic structure layout is overfilled). Typically such a target is measured using dark field scatterometry in which the zeroth order of diffraction (corresponding to a specular reflection) is blocked, and only higher orders processed. Examples of dark field metrology can be found in PCT patent application publication nos. WO 2009/078708 and WO 2009/106279, which are hereby incorporated in their entirety by reference. Further developments of the technique have been described in U.S. patent application publications US2011-0027704, US2011-0043791 and US2012-0242970, which are hereby incorporated in their entirety by reference. Diffraction-based overlay using dark-field detection of the diffraction orders enables overlay measurements on smaller targets. These targets can be smaller than the illumination spot and may be surrounded by product structures on a substrate. In an embodiment, multiple targets can be measured in one image.

An embodiment of a dark field metrology apparatus is shown in FIG. 3(a). A target T (comprising a periodic structure) and diffracted rays are illustrated in more detail in FIG. 3(b). The dark field metrology apparatus may be a stand-alone device or incorporated in either the lithographic apparatus LA, e.g., at the measurement station, or the lithographic cell LC. An optical axis, which has several branches throughout the apparatus, is represented by a dotted line O. In this apparatus, radiation emitted by an output 11 (e.g., a source such as a laser or a xenon lamp or an opening connected to a source) is directed onto substrate W via a prism 15 by an optical system comprising lenses 12, 14 and objective lens 16. These lenses are arranged in a double sequence of a 4F arrangement. A different lens arrangement can be used, provided that it still provides a substrate image onto a detector.

In an embodiment, the lens arrangement allows for access of an intermediate pupil-plane for spatial-frequency filtering. Therefore, the angular range at which the radiation is incident on the substrate can be selected by defining a spatial intensity distribution in a plane that presents the spatial spectrum of the substrate plane, here referred to as a (conjugate) pupil plane. In particular, this can be done, for example, by inserting an aperture plate 13 of suitable form between lenses 12 and 14, in a plane which is a back-projected image of the objective lens pupil plane. In the example illustrated, aperture plate 13 has different forms, labeled 13N and 13S, allowing different illumination modes to be selected. The illumination system in the present examples forms an off-axis illumination mode. In the first illumination mode, aperture plate 13N provides off-axis illumination from a direction designated, for the sake of description only, as 'north'. In a second illumination mode, aperture plate 13S is used to provide similar illumination, but from a different (e.g., opposite) direction, labeled 'south'. Other modes of illumination are possible by using different apertures. The rest of the pupil plane is desirably dark as any unnecessary radiation outside the desired illumination mode may interfere with the desired measurement signals.

As shown in FIG. 3(b), target T is placed with substrate W substantially normal to the optical axis O of objective lens 16. A ray of illumination I impinging on target T from an angle off the axis O gives rise to a zeroth order ray (solid line 0) and two first order rays (dot-chain line +1 and double dot-chain line −1). With an overfilled small target T, these rays are just one of many parallel rays covering the area of the substrate including metrology target T and other features. Where a composite periodic structure target is provided, each individual periodic structure within the target will give rise to its own diffraction spectrum. Since the aperture in plate 13 has a finite width (necessary to admit a useful quantity of radiation), the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown. Note that the periodic structure pitch and illumination angle can be designed or adjusted so that the first order rays entering the objective lens are closely aligned with the central optical axis. The rays illustrated in FIGS. 3(a) and 3(b) are shown somewhat off axis, purely to enable them to be more easily distinguished in the diagram.

At least the 0 and +1 orders diffracted by the target on substrate W are collected by objective lens 16 and directed back through prism 15. Returning to FIG. 3(a), both the first and second illumination modes are illustrated, by designating diametrically opposite (in this case) apertures labeled as north (N) and south (S). When the incident ray I is from the north side of the optical axis, that is when the first illumination mode is applied using aperture plate 13N, the +1 diffracted rays, which are labeled +1(N), enter the objective lens 16. In contrast, when the second illumination mode is applied using aperture plate 13S the −1 diffracted rays (labeled −1(S)) are the ones which enter the lens 16. Thus, in an embodiment, measurement results are obtained by measuring the target twice under certain conditions, e.g., after rotating the target or changing the illumination mode or changing the imaging mode to obtain separately the −1$^{st}$ and the +1$^{st}$ diffraction order intensities. Comparing these intensities for a given target provides a measurement of asymmetry in the target, and asymmetry in the target can be used as an indicator of a parameter of a lithography process, e.g., overlay error. In the situation described above, the illumination mode is changed.

A beam splitter 17 divides the diffracted beams into two measurement branches. In a first measurement branch, optical system 18 forms a diffraction spectrum (pupil plane image) of the target on first sensor 19 (e.g. a CCD or CMOS sensor) using the zeroth and first order diffractive beams. Each diffraction order hits a different point on the sensor, so that image processing can compare and contrast orders. The pupil plane image captured by sensor 19 can be used for focusing the metrology apparatus and/or normalizing intensity measurements of the first order beam. The pupil plane image can also be used for asymmetry measurement as well as for many measurement purposes such as reconstruction, which are not described in detail here. The first examples to be described will use the second measurement branch to measure asymmetry.

In the second measurement branch, optical system 20, 22 forms an image of the target on the substrate W on sensor 23 (e.g. a CCD or CMOS sensor). In the second measurement branch, an aperture stop 21 is provided in a plane that is conjugate to the pupil-plane. Aperture stop 21 functions to block the zeroth order diffracted beam so that the image DF of the target formed on sensor 23 is formed from the −1 or +1 first order beam. The images captured by sensors 19 and 23 are output to image processor and controller PU, the function of which will depend on the particular type of measurements being performed. Note that the term 'image' is used here in a broad sense. An image of the features of a periodic structure of the target as such will not be formed, if only one of the −1 and +1 orders is present.

The particular forms of aperture plate 13 and stop 21 shown in FIG. 3 are purely examples. In another embodiment, on-axis illumination of the targets is used and an aperture stop with an off-axis aperture is used to pass substantially only one first order of diffracted radiation to the sensor (the apertures shown at 13 and 21 are effectively swapped in that case). In yet other embodiments, 2nd, 3rd and higher order beams (not shown in FIG. 3) can be used in measurements, instead of or in addition to the first order beams.

In order to make the illumination adaptable to these different types of measurement, the aperture plate 13 may comprise a number of aperture patterns formed around a disc, which rotates to bring a desired pattern into place. Alternatively or in addition, a set of plates 13 could be provided and swapped, to achieve the same effect. A programmable illumination device such as a deformable mirror array or transmissive spatial light modulator can be used also. Moving mirrors or prisms can be used as another way to adjust the illumination mode.

As just explained in relation to aperture plate 13, the selection of diffraction orders for imaging can alternatively be achieved by altering the aperture stop 21, or by substituting a pupil-stop having a different pattern, or by replacing the fixed field stop with a programmable spatial light modulator. In that case the illumination side of the measurement optical system can remain constant, while it is the imaging side that has first and second modes. In practice, there are many possible types of measurement method, each with its own advantages and disadvantages. In one method, the illumination mode is changed to measure the different orders. In another method, the imaging mode is changed. In a third method, the illumination and imaging modes remain unchanged, but the target is rotated through, e.g., 180 degrees. In each case the desired effect is the same, namely to select first and second portions of the non-zero order diffracted radiation which are, e.g., symmetrically opposite one another in the diffraction spectrum of the target.

While the optical system used for imaging in the present examples has a wide entrance pupil which is restricted by the aperture stop 21, in other embodiments or applications the entrance pupil size of the imaging system itself may be small enough to restrict to the desired order, and thus serve also as the field stop. Different aperture plates are shown in FIGS. 3(c) and (d) which can be used as described further below.

Typically, a target will be aligned with its periodic structure features running either north-south or east-west. That is to say, a periodic structure (e.g., grating) will be aligned in the X direction or the Y direction of the substrate W. But, it may be angled at a different angle, i.e., at 45°. Aperture plate 13N or 13S is used to measure a periodic structure of a target oriented in one direction (e.g., X, Y or other direction depending on the set-up). For measurement of a periodic structure at another angle (e.g., substantially orthogonal), rotation of the target might be implemented (e.g., rotation through 90° and 270° for substantially orthogonal periodic structures). Or, illumination from another angle (e.g., east or west) may be provided in the illumination optics, using the aperture plate 13E or 13W, shown in FIG. 3(c), which may have the apertures at the appropriate angle (e.g., east or west). The aperture plates 13N to 13 W can be separately formed and interchanged, or they may be a single aperture plate which can be rotated by appropriate angle (e.g., 90, 180 or 270 degrees).

Different aperture plates are shown in FIGS. 3(c) and (d). FIG. 3(c) illustrates two further types of off-axis illumination mode. In a first illumination mode of FIG. 3(c), aperture plate 13E provides off-axis illumination from a direction designated, for the sake of description only, as 'east' relative to the 'north' previously described. As noted above, the 'east' may be at a different angle than as shown. In a second illumination mode of FIG. 3(c), aperture plate 13W is used to provide similar illumination, but from a different (e.g., opposite) direction, labeled 'west'. FIG. 3(d) illustrates two further types of off-axis illumination mode. In a first illumination mode of FIG. 3(d), aperture plate 13NW provides off-axis illumination from the directions designated 'north' and 'west' as previously described. In a second illumination mode, aperture plate 13SE is used to provide similar illumination, but from a different (e.g., opposite) direction, labeled 'south' and 'east' as previously described. Provided that crosstalk between these different diffraction signals is not too great, measurements of periodic structures extending in different directions (e.g., both X and Y) can be performed without changing the illumination mode. The use of these, and numerous other variations and applications of the apparatus are described in, for example, the prior published patent application publications mentioned above. As mentioned already, the off-axis apertures illustrated in FIGS. 3(c) and (d) could be provided in the aperture stop 21 instead of in aperture plate 13. In that case, the illumination would be on axis.

FIG. 4 depicts an example composite metrology target formed on a substrate. The composite target comprises four periodic structures (e.g., gratings) 32, 33, 34, 35 positioned closely together. In an embodiment, the periodic structures are positioned closely together enough so that they all are within a measurement spot 31 formed by the illumination beam of the metrology apparatus. In that case, the four periodic structures thus are all simultaneously illuminated and simultaneously imaged on sensors 19 and 23. In an example dedicated to overlay measurement, periodic structures 32, 33, 34, 35 are themselves composite periodic structures formed by overlying periodic structures of another target that is patterned in a different layer of the device formed on substrate W. Such a target may have outer dimensions within 20 µm×20 µm or within 16 µm×16 µm. Further, all the periodic structures are used to measure overlay between a particular pair of layers. To facilitate a target being able to measure more than a single pair of layers, periodic structures 32, 33, 34, 35 may have differently biased overlay offsets in order to facilitate measurement of overlay between different layers in which the different parts of the composite periodic structures are formed. Thus, all the periodic structures for the target on the substrate would be used to measure one pair of layers and all the periodic structures for another same target on the substrate would be used to measure another pair of layers, wherein the overlay bias facilitates distinguishing between the layer-pairs. The meaning of overlay bias will be explained below, particularly with reference to FIG. 7.

FIGS. 7(a)-(c) show schematic cross sections of overlay periodic structures of respective targets T, with different biases. These can be used on substrate W, as seen in FIGS. 3 and 4. Periodic structures with periodicity in the X direction are shown for the sake of example only. Different combinations of these periodic structures with different biases and with different orientations can be provided.

Starting with FIG. 7(a), a composite overlay target 600 formed in two layers, labeled L1 and L2, is depicted. In the lower layer L1, a first periodic structure is formed by features (e.g., lines) 602 and spaces 604 on a substrate 606. In layer L2, a second periodic structure is formed by features (e.g., lines) 608 and spaces 610. (The cross-section is drawn such that the features 602, 608 extend into the page.) The periodic structure pattern repeats with a pitch P in both layers. Lines 602 and 608 are mentioned for the sake of example only, other types of features such as dots, blocks and via holes can be used. In the situation shown at FIG. 7(a), there is no overlay error and no bias, so that each periodic structure feature 608 lies exactly over a periodic structure feature 602 in the lower periodic structure.

At FIG. 7(b), the same target with a bias +d is depicted such that the features 608 of the upper periodic structure are shifted by a distance d to the right, relative to the features 602 of the lower periodic structure. That is, features 608 and features 602 are arranged so that if they were both printed exactly at their nominal locations, features 608 would be offset relative to the features 602 by the distance d. The bias distance d might be a few nanometers in practice, for example 5-60 nm, while the pitch P is for example in the range 300-1000 nm, for example 500 nm or 600 nm. At FIG. 7(c), the same target with a bias −d is depicted such that the features 608 are shifted to the left relative to the features 602. Biased targets of this type shown at FIG. 7(a) to (c) are described in, for example, the patent application publications mentioned above.

Further, while FIGS. 7(a)-(c) depicts the features 608 lying over the features 602 (with or without a small bias of +d or −d applied), which is referred to as a "line on line" target having a bias in the region of zero, a target may have a programmed bias of P/2, that is half the pitch, such that each feature 608 in the upper periodic structure lies over a space 604 in the lower periodic structure. This is referred to as a "line on trench" target. In this case, a small bias of +d or −d may also be applied. The choice between "line on line" target or a "line on trench" target depends on the application.

Returning to FIG. 4, periodic structures 32, 33, 34, 35 may also differ in their orientation, as shown, so as to diffract incoming radiation in X and Y directions. In one example, periodic structures 32 and 34 are X-direction periodic structures with biases of +d, −d, respectively. Periodic structures 33 and 35 may be Y-direction periodic structures with offsets +d and −d respectively. While four periodic structures are illustrated, another embodiment may include a larger matrix to obtain desired accuracy. For example, a 3×3 array of nine composite periodic structures may have biases −4d, −3d, −2d, −d, 0, +d, +2d, +3d, +4d. Separate images of these periodic structures can be identified in the image captured by sensor 23.

FIG. 5 shows an example of an image that may be formed on and detected by the sensor 23, using the target of FIG. 4 in the apparatus of FIG. 3, using the aperture plates 13NW or 13SE from FIG. 3(d). While the sensor 19 cannot resolve the different individual periodic structures 32 to 35, the sensor 23 can do so. The cross-hatched rectangle represents the field of the image on the sensor, within which the illuminated spot 31 on the substrate is imaged into a corresponding circular area 41. In an embodiment, the field is dark. Within this image, rectangular areas 42-45 represent the images of the periodic structures 32 to 35. If the periodic structures are located in product areas, product features may also be visible in the periphery of this image field. While only a single composite grating target is shown in the dark field image of FIG. 5, in practice a product made by lithography may have many layers, and overlay measurements are desired to be made between different pairs of layers. For each overlay measurement between pair of layers, one or more composite grating targets are used, and therefore other composite targets may be present within the image field. Image processor and controller PU processes these images using pattern recognition to identify the separate images 42 to 45 of periodic structures 32 to 35. In this way, the images do not have to be aligned very precisely at a specific location within the sensor frame, which greatly improves throughput of the measuring apparatus as a whole.

Once the separate images of the periodic structures have been identified, the intensities of those individual images can be measured, e.g., by averaging or summing selected pixel intensity values within the identified areas. Intensities and/or other properties of the images can be compared with one another. These results can be combined to measure different parameters of the patterning process. Overlay performance is an example of such a parameter. For example, comparing the intensities reveals asymmetries that can be used as a measure of overlay. In another technique for measuring asymmetry and hence overlay, the sensor 19 is used.

FIG. 6 illustrates how, using for example the method described in PCT patent application publication no. WO 2011/012624 and U.S. patent application publication no. 2011/027704 and using for example the apparatus of FIGS. 3 and 4, overlay error between the two layers containing the component periodic structures 32 to 35 is measured through asymmetry of the periodic structures, as revealed by comparing their intensities in the +1 order and −1 order dark field images.

At step M1, the substrate, for example a semiconductor wafer, is processed through the lithographic cell of FIG. 2 one or more times, to create a structure including the target comprising periodic structures 32-35 that form a metrology target. At M2, using the metrology apparatus of FIG. 3, an image of the periodic structures 32 to 35 is obtained using one of the first order diffracted beams (say −1). In an embodiment, a first illumination mode (e.g., the illumination mode created using aperture plate 13NW) is used. Then, whether by changing the illumination mode, or changing the imaging mode, or by rotating substrate W by 180° in the field of view of the metrology apparatus, a second image of the periodic structures using the other first order diffracted beam (+1) can be obtained (step M3). Consequently, the +1 diffracted radiation is captured in the second image. In an embodiment, the illuminated mode is changed and a second illumination mode (e.g., the illumination mode created using aperture plate 13SE) is used. It is a matter of design choice whether all the periodic structures can be captured in each image, or whether there needs to be relative movement between the measurement apparatus and the substrate so as to capture the periodic structures in separate images. In either case, it is assumed that first and second images of all the component periodic structures are captured via sensor 23.

Note that, by including only half of the first order diffracted radiation in each image, the 'images' referred to here are not conventional dark field microscopy images. The individual periodic structure features are not resolved, because only one of the +1 and −1 order diffracted radiation is present. Each periodic structure will be represented simply by an area of a certain intensity level. In step M4, a region of interest (ROI) is identified within the image of each component periodic structure, from which intensity levels will be measured. This is done because, particularly around the edges of the individual grating images, intensity values can be highly dependent on process variables such as resist thickness, composition, line shape, as well as edge effects generally.

Having identified the region of interest P1, P2, P3, P4 for each respective individual periodic structure 32-35 and measured its intensity, the asymmetry of the periodic structure, and hence, e.g., overlay error, can then be determined. This is done by the image processor and controller PU in step M5 comparing the intensity values obtained for +1 and −1 orders for each periodic structure 32-35 to identify any difference in their intensity, i.e., an asymmetry. The term "difference" is not intended to refer only to subtraction. Differences may be calculated in ratio form. Thus, the intensity difference is calculated at step M5 to obtain a measurement of asymmetry for each periodic structure. In step M6 the measured asymmetries for a number of periodic structures are used together with, if applicable, knowledge of the overlay biases of those periodic structures to calculate one or more performance parameters of the patterning process in the vicinity of the target T. A performance parameter of interest may be overlay. Other parameters of performance of the patterning process can be calculated such as focus and/or dose. The one or more performance parameters can be fed back for improvement of the patterning process, and/or used to improve the measurement and calculation process of FIG. 6 itself.

Figure 8:
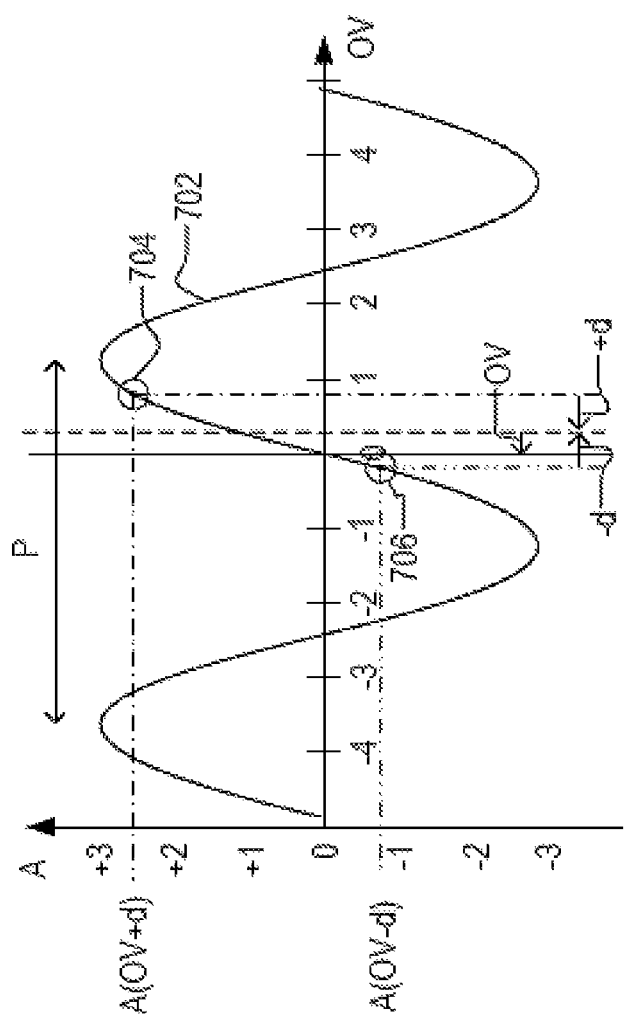
FIG. 8 illustrates principles of overlay measurement in an ideal target structure.

In an embodiment to determine overlay, FIG. 8 depicts a curve 702 that illustrates the relationship between overlay error OV and measured asymmetry A for an 'ideal' target having zero offset and no feature asymmetry within the individual periodic structures forming the overlay periodic structure. This graph is to illustrate the principles of determining the overlay only, and in the graph, the units of measured asymmetry A and overlay error OV are arbitrary.

In the 'ideal' situation of FIGS. 7(a)-(c), the curve 702 indicates that the measured asymmetry A has a sinusoidal relationship with the overlay. The period P of the sinusoidal variation corresponds to the period (pitch) of the periodic structures, converted of course to an appropriate scale. The sinusoidal form is pure in this example, but can include harmonics in real circumstances. For the sake of simplicity, it is assumed in this example (a) that only first order diffracted radiation from the target reaches the image sensor 23 (or its equivalent in a given embodiment), and (b) that the experimental target design is such that within these first orders a pure sine-relation exists between intensity and overlay between top and lower periodic structures results. Whether this is true in practice is a function of the optical system design, the wavelength of the illuminating radiation and the pitch P of the periodic structure, and the design and stack of the target.

As mentioned above, biased periodic structures can be used to measure overlay, rather than relying on a single measurement. This bias has a known value defined in the patterning device (e.g. a reticle) from which it was made, that serves as an on-substrate calibration of the overlay corresponding to the measured signal. In the drawing, the calculation is illustrated graphically. In steps M1-M5 of FIG. 6, asymmetry measurements A(+d) and A(−d) are obtained for component periodic structures having biases +d and −d respectively (as shown in FIGS. 7(b) and 7(c), for example). Fitting these measurements to the sinusoidal curve gives points 704 and 706 as shown. Knowing the biases, the true overlay error OV can be calculated. The pitch P of the sinusoidal curve is known from the design of the target. The vertical scale of the curve 702 is not known to start with, but is an unknown factor which we can call a $1^{st}$ harmonic proportionality constant, $K_1$.

In equation terms, the relationship between overlay and asymmetry is assumed to be:

$$A = K_1 \cdot \sin(OV)$$

where OV is expressed on a scale such that the periodic structure pitch P corresponds to an angle $2\pi$ radians. Using two measurements with periodic structures with different, known biases one can solve two equations to calculate the unknowns $K_1$ and overlay OV.

Thus, in general, for an overlay target comprising overlaying periodic structures (i.e., a periodic structure in each of a plurality of layers and at least one periodic structure spaced apart from overlying at least partially at least one lower periodic structure), the diffracted intensity of incident radiation on the overlay target is determined by the amplitude diffraction coefficients of both the upper and lower periodic structures, and the phase difference between waves diffracted at the upper periodic structure and diffracted at the lower periodic structure. When one of the periodic structures is shifted relative to the other in terms of overlying each other (e.g., horizontally), an additional phase shift is introduced that is opposite for the +1 and −1 orders. This causes an intensity difference in the two 1st order diffraction intensities. As discussed above, the intensity asymmetry (the difference in intensity between +1 and −1 diffraction orders) is proportional to overlay (A=K*OV). So, by measuring the asymmetry on two different periodic structures with two different imposed additional shifts (biases +d and −d of, e.g., +20 and −20 nm), the proportionality constant (K) can be determined, and the overlay (OV) can be determined.

Many aspects of the target, the measurement apparatus and the measurement method are significant to achieving good results. For example, there should be good "detectability" e.g., a high signal to noise ratio. This is to a significant extent determined by the diffraction efficiency (the ratio of the amount of the desired (usually the first order) diffracted radiation and the illumination beam) and the stack sensitivity (a measurement of how much the intensity of the signal changes as overlay changes because of relative change in the amount of radiation per unit amount of overlay) of the target. There should be good "accuracy". This implies, for example, that the measurement should be relatively insensitive to process induced variation, e.g., process induced structural asymmetry in the lower or upper periodic structure of the target (e.g., a change in sidewall angle, a change in bottom wall angle, etc.). Both detectability and accuracy are desirably optimized by creating and choosing the right target design, and by selecting the right measurement settings (e.g., the wavelength and/or polarization of the illumination beam). Thus, a metrology target design can be characterized by various parameters such as, for example, target coefficient (TC), stack sensitivity (SS), overlay impact (OV), or the like. Target coefficient can be understood as a measurement of signal-to-noise ratio for a particular measurement time as a result of variations in photon collection by the measurement system. In an embodiment, the target coefficient can also be thought of as the ratio of stack sensitivity to photon noise; that is, the signal (i.e., the stack sensitivity) may be divided by a measurement of the photon noise to determine the target coefficient. Overlay impact measures the change in overlay error as a function of target design.

In practice, materials and layer thicknesses are chosen to optimize the yield and performance of the devices to be manufactured on the substrate, and not to optimize the performance of the metrology target. In combination with other restrictions, such as design rules, it is sometimes difficult, or even impossible, to obtain a "good" target/recipe combination. As an example, if the layer in between an upper and lower periodic structure of a target is absorbing, the amount of radiation coming from the lower periodic structure may be significantly weaker than the radiation coming from the upper periodic structure. As a consequence, the target can be "bright" when measured by a detector, but the overlay sensitivity may be small, and so proper determination of overlay may be difficult.

Furthermore, the target design may be based on a nominal stack (i.e., the combination of layers and materials in which the measured periodic structures are formed) that, e.g., was used in a simulation model. However, a "real" stack may be different than the nominal stack, and/or may vary due to variations in the patterning process. This, and possible variation in the measurement process, makes it such the target response may be quite different (typically worse) from what was expected (e.g., simulated) and so making it difficult to find a suitable metrology target design and measurement recipe. This is further exacerbated by the fact that typically once the metrology target design has been put on the patterning device it cannot be changed until a new patterning device is created and changes in measurement recipe may not be sufficient to enable good measurement/determination of a parameter of interest.

Further, although a range of wavelengths may be available for the illumination beam in a measurement, the optics of the measurement apparatus may have a "sweet spot", a wavelength range where the performance is better than for other wavelengths. But, this "sweet spot" may not coincide with the wavelength range that the metrology target should desirably have to enable good measurement/determination of a parameter of interest.

In a typical metrology target, an upper periodic structure (e.g., a grating) at least partially overlaps a lower periodic structure (e.g., a grating). Further, when measured using a measurement apparatus, both of those periodic structures are illuminated by a single measurement beam. And, the upper and lower periodic structures have a substantially same pitch such that the outgoing diffracted radiation of the upper and lower periodic structures combine into a single beam (per diffraction order). To address one or more of the issues identified above, or other issues, there is proposed a different metrology target design, measurement apparatus and measurement process.

According to an embodiment, an upper periodic structure (e.g., grating) is illuminated by a different measurement beam than a lower periodic structure (e.g., grating). Thus, the different measurement beams may be controlled independently. Further, in an embodiment, those different measurement beams are coherent with each other (i.e., have a substantially fixed phase relation) and provided such that they do not substantially interfere with each other before diffraction by the respective periodic structures. Then, the diffracted radiation from the upper and lower periodic structures are combined into a single optical beam, such that the diffracted radiation from the upper and lower periodic structures can interfere and carry overlay information. The combined diffracted beam can be detected and analyzed in either the pupil plane (e.g., pupil based overlay determination) or in a field plane (e.g. in a dark field image). A metrology target design, described further below, is provided that enables these steps.

By controlling the intensity ratio and/or phase difference of the radiation going to the upper and lower periodic structures, it becomes possible to effectively control the response of the metrology target. For example the stack sensitivity, robustness to process variation, and/or the sensitivity to structural asymmetry of the lower periodic structure asymmetry can be adjusted. Therefore, in an embodiment, measurement performance may be optimized beyond what is currently possible. Additionally or alternatively, the application space can be enlarged.

Figure 9:
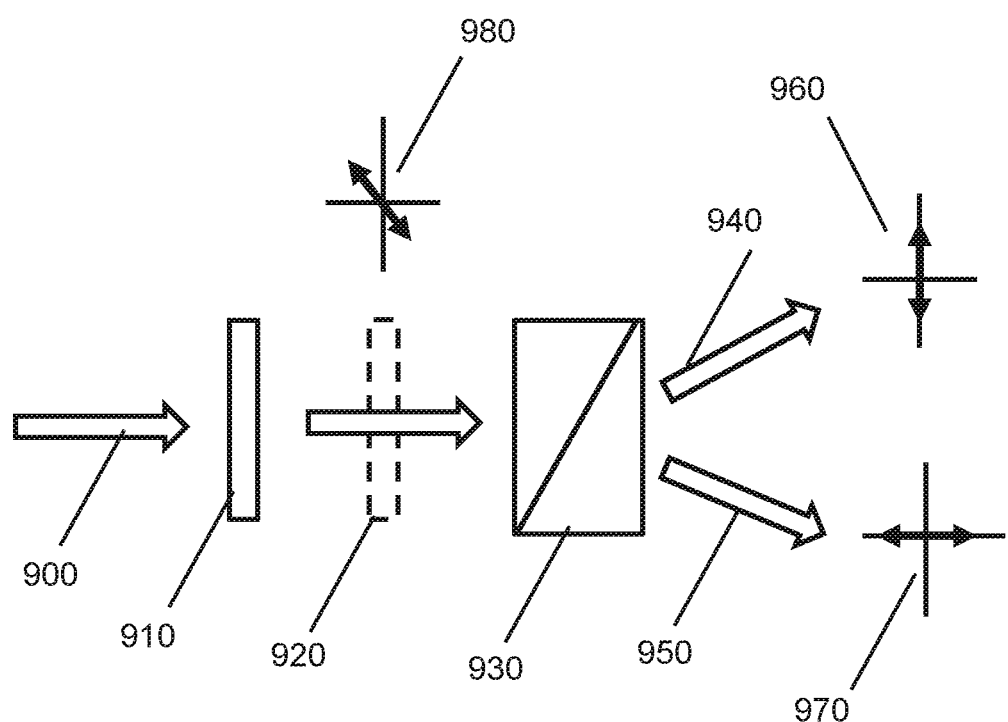
FIG. 9 schematically depicts an embodiment of an optical system design for a measurement apparatus.

According to an embodiment, at least two separate illuminating beams with perpendicular polarization are used. In this way, the illumination beams cannot interfere (interference could cause e.g. a stripe pattern to illuminate the target instead of a uniform spot). Referring to FIG. 9, an embodiment of an optical system to enable providing such beams is schematically depicted. The optical system receives an incoming beam 900 from, e.g., a lamp or a fiber (not shown merely for convenience), which beam is provided to a polarizer or retarder 910. The beam from the polarizer or retarder 910 may optionally be provided to a compensator 920. Whether from polarizer or retarder 910 or an optional compensator 920, the polarized radiation is then provided to a beam splitter 930. In an embodiment, the beam splitter 930 is a polarizing beam splitter or a Wollaston or Nomarski prism. From beam splitter 930, a first polarized beam 940 and a separate second polarized beam 950 are provided. The first and second polarized beams 940, 950 are orthogonally polarized. For example, the first beam 940 may have, as shown at 960, a linear polarization in a first direction and the second beam 950 may have, as shown at 970, a linear polarization in a second direction orthogonal to the first direction. For example, the polarization directions can be chosen along 0 and 90 degrees (as shown in FIG. 9), but they can be rotated, e.g. by rotating the entire unit in FIG. 9. In an embodiment, the polarizations are chosen to be +45 and −45 degrees with respect to the direction of elongation of features of the periodic structures of the target; in that case, the interaction with the target will be substantially identical for the beams 940, 950. While in this example linearly polarized beams 940, 950 are used, an embodiment may use different polarizations (e.g. left-handed circular polarization and right-handed circular polarization), as long as the polarizations of the beams 940, 950 are orthogonal. In order to help ensure the first and second beams 940, 950 have a substantially fixed phase relation the incoming beam 900 should, as shown at 980, be polarized at an angle in between the respective polarizations of the first and second beams 940, 950 (e.g. at 45 degrees with these polarizations).

By varying the position (e.g., rotation angle) of the polarization direction at incoming polarizer or retarder 910, the intensity ratio of the beams 940, 950 can be controlled. Further, if the optional compensator (e.g. a retarder, such as a quarter waveplate) is provided between the polarizer or retarder 910 and the beam splitter 930, the phase difference between the beams 940, 950 can be varied. Once the beams 940, 950 have been created, any optical design can be used to direct the beams 940, 950 each to their own pupil and/or field position.

Now, in an embodiment, there is provided a configuration of these beams 940, 950, an associated metrology target design, and a way to recombine the diffracted radiation from the beams 940, 950.

Figure 10A:
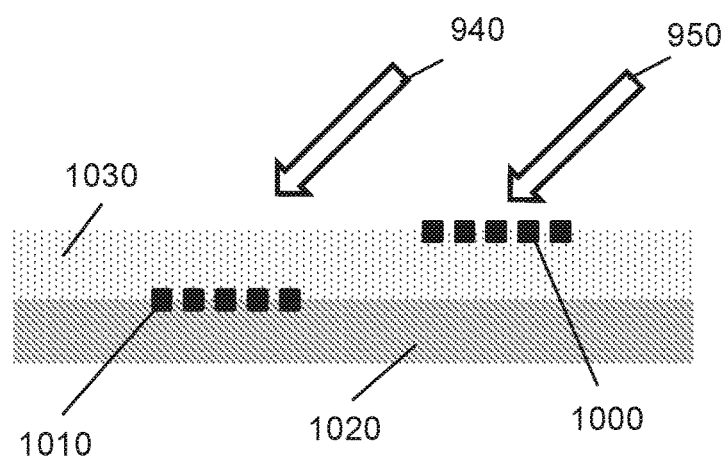
FIG. 10A schematically depicts a side view of an embodiment of a metrology target in the layers of a substrate and incident measurement radiation beams.

Referring to FIG. 10, an embodiment of a metrology target along with incident measurement beams is schematically depicted. Referring to FIG. 10A, as compared to a typical diffraction-based metrology target, two measurement beams 940, 950, instead of one measurement beam, are provided, each beam with the substantially same angle of incidence on its respective periodic structure 1000, 1010 of the metrology target. Further, the periodic structures do not overlie each other fully. The lower periodic structure and the upper periodic structure are laterally displaced by the substantially same distance as the measurement beams 940, 950 are laterally displaced—see FIG. 10A. As shown in FIG. 10A, beam 950 illuminates periodic structure 1000 and beam 940 illuminates different periodic structure 1010, where periodic structure 1010 is in a lower layer 1020 and periodic structure 1000 is in an upper layer 1030. Since each beam 940, 950 illuminates a respective one of the periodic structures 1010, 1000, each periodic structure 1000, 1010 will provide its own diffracted beam of radiation.

In an embodiment, the splitting plane of the beam splitter 930 (e.g., a Wollaston or Nomarski prism) that splits the illumination beam 900 coincides with an equivalent pupil plane. In this way, both beams 940, 950 originate from a substantially same pupil point, but are shifted with respect to each other in the field plane. Thus, two different spots—see, e.g., spots of the beams 940, 950 in FIG. 10B—are created on the target.

Figure 10B:
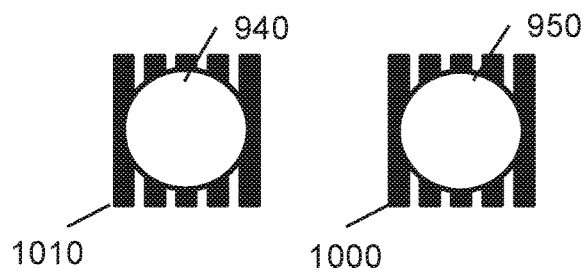
FIG. 10B schematically depicts a top view of the metrology target and incident radiation beams of FIG. 10A.
Figure 11A:
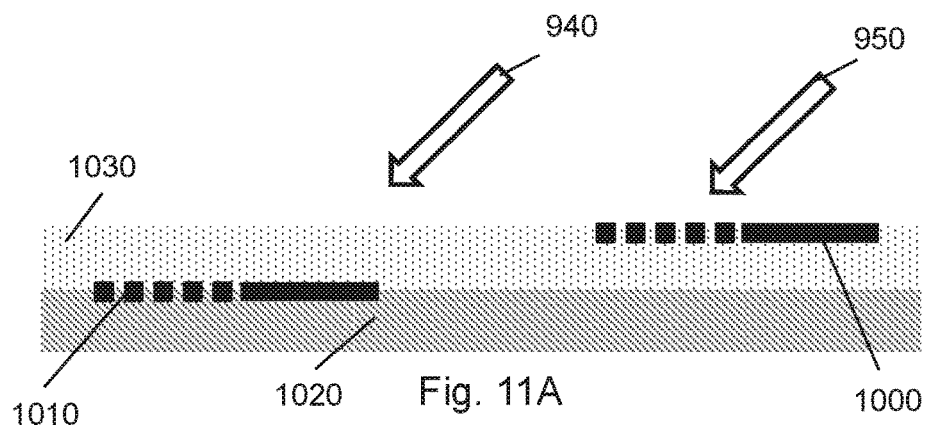
FIG. 11A schematically depicts a side view of an embodiment of a metrology target in the layers of a substrate and incident measurement radiation beams.
Figure 11B:
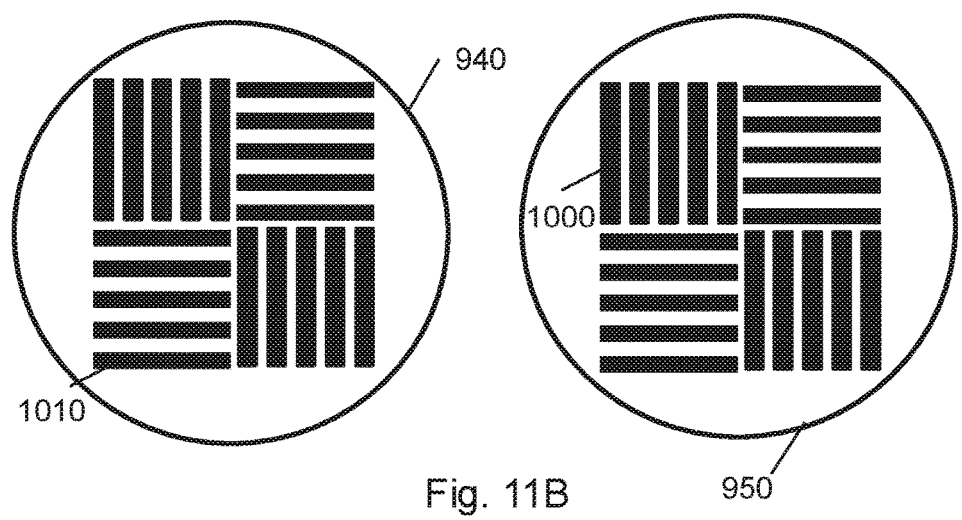
FIG. 11B schematically depicts a top view of the metrology target and incident radiation beams of FIG. 11A.

In an embodiment, "underfill" spots (i.e., the respective spot is contained within the boundary of its respective periodic structure) as depicted in FIG. 10B are measured in pupil mode. In an embodiment, other measurement modes can be supported. For example, a (dark-) field image can be obtained instead of a pupil image. This can be combined with an "overfill" spot (i.e., the respective spot extends beyond the boundary of its respective periodic structure) as depicted in FIG. 11B. So, like FIG. 10, the target in FIG. 11 is provided in separate parts, a periodic structure 1000 in the upper layer 1030 and a periodic structure 1010 in a lower layer 1020. In FIG. 11, the spacing between the spots of the beams 940, 950 (and thus the periodic structures 1000, 1010 of the target) is larger than the spot size itself, and thus the spots are clearly separated.

Further, FIG. 10 depicts an example of periodic structures in the form of single gratings while FIG. 11 depicts an example of the periodic structures in the form a combination of gratings (in the example of FIG. 11, gratings with orthogonal directions of elongation of the features of the gratings). But, the periodic structures of FIG. 11 may be used in the embodiment of FIG. 10. So, embodiments herein can have periodic structures having, e.g., a single kind of periodic structure (e.g., a grating), periodic structures having, e.g., a plurality of periodic structures (e.g., gratings), which periodic structures may have a direction of elongation of features at different angles from each other, and/or a combination thereof.

In order to determine, e.g., overlay, the diffracted radiation from the illumination of the periodic structures 1000, 1010 with the respective beams 950, 940 should interfere, and so need to be recombined. For this recombination, a similar technique as used to split the beam 900 into beams 940, 950 can be used, but in the inverse direction. For example, a combining optical element (e.g., a Wollaston or Nomarski prism) may be provided in the detection path to receive the diffracted radiation with orthogonal polarizations created from the illumination of the periodic structures 1000, 1010 with the respective beams 950, 940 and the combining optical element combines the diffracted radiation into a single beam. This combining optical element is then followed by another polarizer or retarder to help make sure the diffracted radiation with orthogonal polarizations can interfere.

In a desirable embodiment, the combining optical element is the beam splitter 930 to enable both the splitting and combination of the diffracted radiation. For example, a Wollaston or Nomarski prism 930 is provided that creates the beams 940, 950 and combines the diffracted radiation with orthogonal polarizations created from the illumination of the periodic structures 1000, 1010 with the respective beams 950, 940.

In an embodiment, the polarization applied in the illumination and detection paths can be provided by the same one or more optical elements. However, in an embodiment, since it is desirable to optimize the metrology target response by, e.g., varying the polarization angles, it is desirable to have separate polarizers or retarders (see, e.g., FIG. 12), such that optimum and/or customized performance can be obtained.

Figure 12:
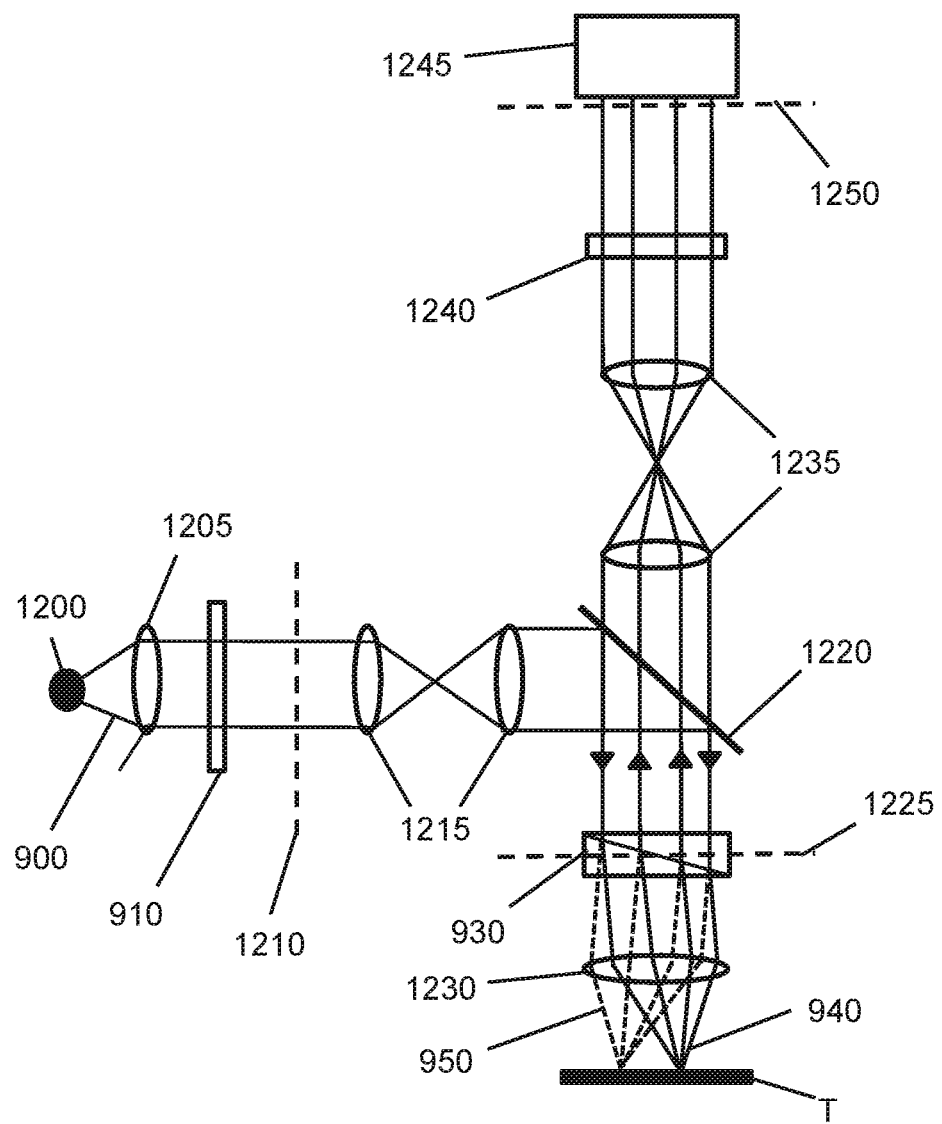
FIG. 12 schematically depicts an embodiment of a measurement apparatus in combination with a metrology target.

Referring to FIG. 12, an embodiment of a measurement apparatus is schematically depicted to enable the creation of the beams 940, 950, combine the diffracted radiation with orthogonal polarizations created from the illumination of the periodic structures 1000, 1010 with the respective beams 950, 940, and to measure the combined diffracted radiation to derive one or more parameters of interest (e.g., overlay). A radiation input 1200, e.g. a lamp or an optical fiber from a radiation source, provides an incoming beam 900. An optional optical element 1205 (e.g., a lens) provides the incoming beam to polarizer or retarder 910. In an embodiment, the incoming beam 900 may be unpolarized and the polarizer 910 provides a desired polarization to the beam. In an embodiment, the incoming beam 900 may be polarized and the retarder 910 changes the polarization to a desired polarization.

The radiation from the polarizer or retarder 910 is provided to a pupil plane (or a conjugate plane thereof) 1210, at or near which may be provided an aperture stop. The radiation from the plane 1210 is then processed by an optional optical element (e.g., a lens system) 1215. Whether from the plane 1210 or the optical element 1215, the radiation, in an embodiment is provided to an optical element 1220 to direct the radiation to a beam splitter 930. In an embodiment, the optical element 1220 may be polarization-sensitive such that it reflects radiation of a certain polarization and allows radiation of a certain different polarization to pass therethrough. In an embodiment, optical element 1220 is in the illumination path for providing beam 900 to the target T and in the detection path of diffracted radiation from the target T.

Optionally, the beam from the polarizer or retarder 910 may be provided to a compensator (not shown in FIG. 12 but see, e.g., compensator 920 in FIG. 9) in the optical path between the polarizer or retarder 910 and the beam splitter 930.

As noted above, the polarized radiation 900 from polarizer or retarder 910 is provided to the beam splitter 930. In an embodiment, the beam splitter 930 is a polarizing beam splitter or a Wollaston or Nomarski prism. In an embodiment, the beam splitting surface of the beam splitter 930 is located or near a pupil plane (or a conjugate plane thereof) 1225. In an embodiment, the beam splitting surface of the beam splitter 930 is located or near a field plane (or a conjugate plane thereof). In this way two different pupil distributions are created (i.e. two different angles of incidence), and a single spot on the substrate. An embodiment of the associated target and the illumination beams will be discussed further above.

From beam splitter 930, a first polarized beam 940 and a separate second polarized beam 950 are provided toward the target T. The first and second polarized beams 940, 950 are orthogonally polarized. For example, the first beam 940 may have a linear polarization in a first direction and the second beam 950 may have a linear polarization in a second direction orthogonal to the first direction. In an embodiment, the polarizations of the first and second beams 940, 950 are chosen to be +45 and −45 degrees with respect to the direction of elongation of features of the periodic structures of the target; in that case, the interaction with the target will be substantially identical for the beams 940, 950. While in this example linearly polarized beams 940, 950 are used, an embodiment may use different polarizations (e.g. left-handed circular polarization and right-handed circular polarization), as long as the polarizations of the beams 940, 950 are orthogonal. In order to help ensure the first and second beams 940, 950 have a substantially fixed phase relation the incoming beam 900 should be polarized at an angle in between the respective polarizations of the first and second beams 940, 950 (e.g. at 45 degrees with these polarizations). An optical element 1230 (e.g., a lens) may provide the beams 940, 950 to the target T.

At target T, the beams 940, 950 are diffracted by the periodic structures of the target T. The diffracted radiation is then provided along a detection path to a detector 1245. As mentioned above, in order to determine, e.g., overlay, the diffracted radiation from the illumination of the periodic structures of target T with the beams 940, 950 should interfere, and so need to be recombined. In an embodiment, a similar technique as used to split the beam 900 into beams 940, 950 can be used, but in the inverse direction. For example, a combining optical element (e.g., a Wollaston or Nomarski prism) may be provided in the detection path to receive the diffracted radiation with orthogonal polarizations created from the illumination of the periodic structures of target T with the beams 940, 950 and the combining optical element combines the diffracted radiation into a single beam. This combining optical element is then followed by another polarizer or retarder 1240 to help make sure the diffracted radiation with orthogonal polarizations can interfere. That is, the polarizer or retarder 1240 in the detection path may be needed to "force" the diffracted radiation beams to interfere if the target T maintains the polarization state (such that even after diffraction they are orthogonal).

In the embodiment of FIG. 12, the combining optical element is the beam splitter 930 to enable both the splitting and combination of the diffracted radiation. For example, a Wollaston or Nomarski prism 930 is provided that creates the beams 940, 950 and combines the diffracted radiation with orthogonal polarizations created from the illumination of the periodic structures of the target T with the beams 940, 950.

In the embodiment of FIG. 12, the optical element 1220 is in the detection path of diffracted radiation from the target T and receives the combined radiation from the beam splitter 930. The optical element 1220 may be polarization-sensitive such that it reflects radiation of the incoming beam 900 and allows diffracted radiation from the target T to pass therethrough. The radiation from the plane beam splitter 930 is then processed by an optional optical element (e.g., a lens system) 1240 and provided to polarizer or retarder 1240. From polarizer or retarder 1240, the radiation is provided to the detector 1245. In an embodiment, the detection surface of the detector receives an image of the pupil plane (or a conjugate plane thereof) 1250.

In an embodiment, the measurement apparatus may comprise an existing measurement apparatus that can be supplemented with a package of the polarizer or retarder 910, polarizer or retarder 1240, and beam splitter 930 (e.g., a Wollaston or Nomarski prism). Thus, the behavior of an existing measurement apparatus can be recovered by, for example, aligning the polarization axes of the polarizers or retarders to the polarization axis of the beam splitter 930, or by removing the beam splitter 930 from the optical path. In an embodiment, the polarizers or retarders 910, 1240 and the beam splitter 930 may be removable from an existing measurement apparatus to leave a working existing measurement apparatus.

In an embodiment, the polarizer or retarder 910 is movable, e.g., rotatable, while in the optical path. In an embodiment, the polarizer or retarder 1240 is movable, e.g., rotatable, while in the optical path. Further, in an embodiment, where provided, compensator 920 is movable, e.g., rotatable, while in the optical path. As discussed above, by varying the position (e.g., rotation angle) of the polarization direction at the polarizer or retarder 910 in the optical path, the intensity ratio of the beams 940, 950 can be controlled. Further, if the optional compensator 920 (e.g. a retarder such as a quarter waveplate) is provided, the phase difference between the beams 940, 950 can be varied.

As was indicated earlier, it is desirable to control the response of the target T. This is achieved by changing the polarization direction or phase retardation in either the illumination or detection path. This can be done mechanically, e.g. by rotating the polarizer or retarder 910, compensator 920 and/or polarizer or retarder 1240. In order to improve the speed, an electro-optical modulator, such as a Pockels cell, may be used.

The settings of polarizer or retarder 910, compensator 920 and/or polarizer or retarder 1240 can be optimized once during an optimization procedure and then kept constant for subsequent measurements. In an embodiment, the settings can be updated dynamically depending on the observed target properties during measurements. In an embodiment, multiple polarizer or retarder 910, compensator 920 and/or polarizer or retarder 1240 settings may be used per target and combined into a single measurement. The choice of settings, whether during optimization or during run time, can be based on the optimization of several parameters, such as stack sensitivity, diffraction efficiency, sensitivity to structural asymmetry of a lower periodic structure, and/or matching to an external reference (such as a SEM).

As should be evident from FIGS. 10 and 11, the target arrangement there takes up more space than a target where a periodic structure in an upper layer fully overlies a periodic structure in a lower layer, since the upper periodic structure is not fully overlying the lower periodic structure. This may be a disadvantage if only, e.g., overlay were measured since an upper periodic structure fully overlying a lower periodic structure could do that while taking less "real estate". But, with this new target arrangement and measurement mode, the lower periodic structure (and/or the upper periodic structure) can be measured separately, for example to monitor structural asymmetry of a periodic structure due to, e.g., process variations. To do so, with a target having an upper periodic structure fully overlying a lower periodic structure, a separate target should be printed, which would now not be needed. Indeed, with a target having an upper periodic structure fully overlying a lower periodic structure, three targets may be needed—one each for the upper periodic structure and the lower periodic structure and one for measuring the parameter of interest, e.g., overlay. In the present arrangement, a single target can be provided with laterally displaced periodic structures as shown in FIGS. 10 and 11, and each of the periodic structures can be monitored on its own as well as a parameter of interest (such as overlay) can be determined using the periodic structures together. For example, using both beams 940, 950, a parameter of interest, such as overlay, can be measured, and using only one of the beam 930, 940 (by, for example, appropriately aligning the polarization axis of the illumination polarizer or retarder 910 to a particular polarization axis of the beam splitter 930) either the lower periodic structure 1010 or the upper periodic structure 1000 can be separately measured.

In the embodiment shown in FIG. 11, the spacing between the spots (and thus the periodic structures of the targets) is larger than the spot size itself, and thus the two spots are separated. However, this is not required. As shown schematically in FIG. 13B, the overfilling spots can also overlap, such that the periodic structures 1000, 1010 of the target can be placed closer together. However, the distance between the centers of the periodic structures 1000, 1010 still should match with the shift between the spot centers. Just in this case, at least part of beam 940 impinges on periodic structure 1000 and at least part of beam 950 impinges on periodic structure 1010.

A simplified version of the arrangement of FIG. 13 is schematically depicted in FIG. 14, where the periodic structures 1000, 1010 respectively comprising a single grating rather than the periodic structures 1000, 1010 depicted in FIG. 13 as comprising a plurality of gratings each. The image that is created on the detector 1245 using the arrangement schematically depicted in FIG. 14 is illustrated in FIG. 15. That is, the resulting image on the detector 1245 after recombining the beams 930, 940 diffracted from the target T after the second pass through the beam splitter 930. While there are two periodic structures of the target, as shown in FIG. 15, the image shows three separate radiation distributions due to the second pass through the beam splitter 930 which recombines the two beams. A first radiation distribution 1500 combines the radiation diffracted by both the upper and lower periodic structures and thus carries, e.g., the 'normal' overlay information. With this combined radiation distribution 1500, a parameter of interest, such as overlay, can be determined. The other radiation distributions—second radiation distribution 1510 and third radiation distribution 1520—respectively provide information on one or more properties (e.g. diffraction efficiency, structural asymmetry, etc.) of the respective individual upper and lower periodic structures 1000, 1010. For example, second radiation distribution 1510 may be associated with periodic structure 1000, while third radiation distribution 1520 may be associated with periodic structure 1010. Advantageously, the information regarding the individual periodic structures can be obtained at the same time/simultaneously with each other and with obtaining the information on the combination of the periodic structures (e.g., overlay information). The determined information from the individual periodic structures or from the combination of the periodic structures can be used to optimize one or more settings or to correct the measurement (e.g., information determined for one or more of the individual periodic structures may be used to correct the information (e.g., overlay) determined from their combination).

Embodiments outlined above have mostly focused on splitting the incoming beam 900 into the beams 940, 950 in the field, such that the beams 940, 950 illuminate at a substantially same angle of incidence at the target and the spots hit the target at different spatial positions. However, in an embodiment, the incoming beam 900 may be split into the beams 940, 950 such that the beams 940, 950 hit a substantially same spot on the target and illuminate the target at different angles of incidence at the target. In this case, the beam 900 may be split into the beams 940, 950 in the pupil. In this fashion, it will still be possible to control the contributions of the plurality of periodic structures separately, yet have an upper periodic structure 1000 fully overlie a lower periodic structure 1010, provided the difference in periodic structure vectors (e.g., periodic structure pitch and/or direction of periodic features) of the periodic structures 1000, 1010 matches with the displacement of the beams 940, 950 in the pupil. In this way, a combined beam can be formed and a parameter of interest (e.g., overlay) can be measured. Thus, this embodiment can have an advantage of having a periodic structure fully overlying another periodic structure but still enable measurement of an individual periodic structure without having another target.

The periodic structure vector thus, in an embodiment, expresses the direction and/or spacing (e.g. pitch) of the periodic features of the periodic structure (e.g., the periodic structure vector points perpendicular to the direction of elongation of the periodic features (e.g., grating lines) and the length scales with $2\pi$/pitch). The periodic structure vector thus determines the diffraction angles of the periodic structure (i.e., positions in pupil space).

Figure 17:
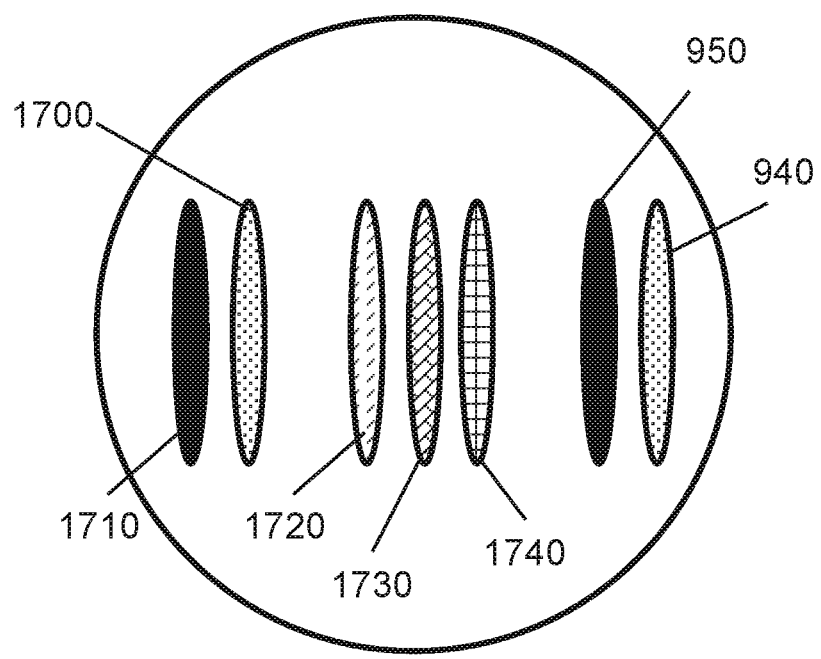
FIG. 17 schematically depicts a measurement of the diffracted radiation from the target of FIG. 16.

FIG. 17 schematically depicts an embodiment using beam separation in the pupil. Two illuminating beams 940, 950 originating from different pupil positions illuminate a target comprising periodic structures 1000, 1010. In this case, the periodic structure 1000 overlies periodic structure 1010 similar to a conventional diffraction target for measuring, for example, overlay. But, the periodic structures 1000, 1010 have a different periodic structure vector (e.g., different pitches and/or different directions of periodic features). And, as shown in FIG. 17, each of the beams 940, 950 illuminate the periodic structures 1000, 1010 at a different angle of incidence. So, both periodic structures each create 1st order beams for each of the beams 940, 950. By making different periodic structure vectors (e.g., the periodic structure pitch and/or periodic feature direction) 'match' to the displacement of the beams in the pupil, i.e., the pupil separation, there will be a plurality of radiation distributions produced, including separate 1st order radiation distributions in the pupil for each periodic structure and for the combination of periodic structures. So, in an embodiment, there is provided a first $1^{st}$ order radiation distribution for one of the periodic structures, a second $1^{st}$ order radiation distribution for a second periodic structure, and a third $1^{st}$ order radiation distribution for the combination of the periodic structures. For example, first $1^{st}$ order radiation distribution 1720 comprises mostly $1^{st}$ order radiation from periodic structure 1010 alone, the second $1^{st}$ order radiation distribution 1740 comprises mostly $1^{st}$ order radiation from periodic structure 1000 alone, and the third $1^{st}$ order radiation distribution 1730 comprises combined $1^{st}$ order radiation from the periodic structures 1000, 1010. Thus, the third $1^{st}$ order radiation distribution 1730 carries, for example, overlay information. The pupil will also contain $0^{th}$ order radiation distributions diffracted from the target from each of the beams 940, 950. Thus, in an embodiment, a first $0^{th}$ order radiation distribution 1700 comprises mostly $0^{th}$ order radiation from beam 950 and a second $0^{th}$ order radiation distribution 1710 comprises mostly $0^{th}$ order radiation from beam 940. Thus, in an embodiment, referring to FIG. 17, the periodic structure vectors (e.g., pitches and/or periodic feature direction) of the periodic structures 1000, 1010 are chosen such that the periodic structures 1000, 1010 are suited for the pupil positions of the illuminating beams 940, 950, and an overlapping area 1730 is formed. Additionally or alternatively, in an embodiment, the pupil positions of the illuminating beams 940, 950 are adapted to the periodic structure vectors (e.g., pitches and/or periodic feature direction) of the periodic structures 1000, 1010.

In this embodiment, the beam splitter 930 can split the radiation into two pupil distributions. But, in this embodiment, the target not only diffracts the radiation but also recombines the diffracted radiation. Thus, the beam splitter 930 or other combiner is not needed in the detection path.

Figure 16:
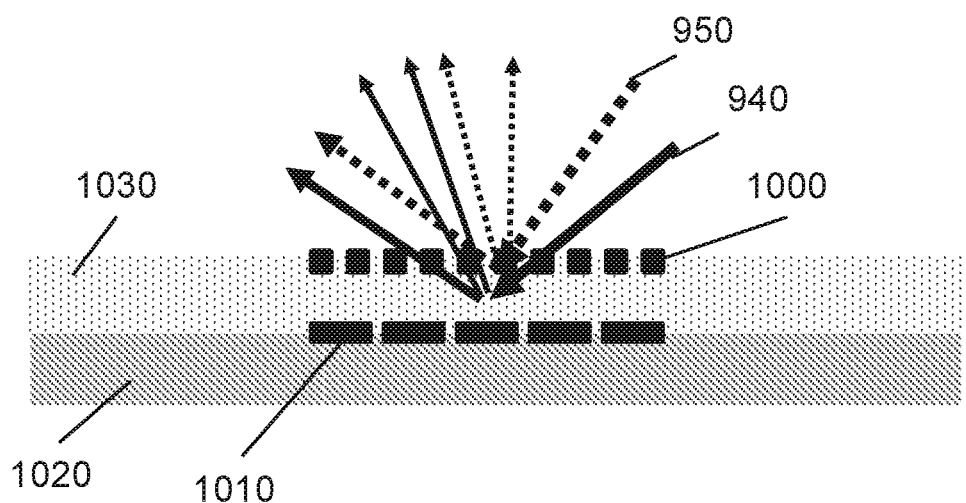
FIG. 16 schematically depicts a side view of an embodiment of a metrology target in the layers of a substrate and incident measurement radiation beams.

Further, while the embodiment shown in FIGS. 16 and 17 shows beams 940, 950 split in the pupil, the same method may be applied in field detection. For example, by using a dark field aperture that transmits only the combined $1^{st}$ order radiation (e.g., the $1^{st}$ order radiation distribution 1730) and imaging the field, an image can be created.

Desirably, a flexible pupil selection can be made (e.g. with a digital micromirror device (DMD) or LCD based 'aperture') such that the contributions of the individual periodic structures can be collected to extract information about, e.g., structural asymmetry of a periodic structure. In an embodiment, a plenoptic camera is used to image all three components simultaneously.

In an embodiment, multiple programmed overlay biases (as discussed above) may be present in the upper and/or lower periodic structures in order to, e.g., calibrate the overlay value.

Figure 18:
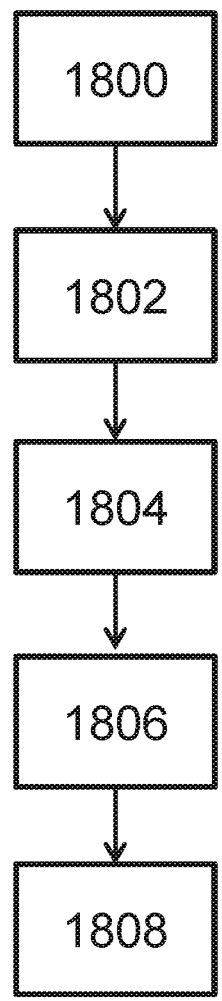
FIG. 18 depicts a flowchart illustrating an embodiment of a metrology method.

So, referring to FIG. 18, an embodiment of a metrology method is presented. At 1800, at least a first periodic structure of a metrology target is illuminated with a first radiation beam having a first polarization.

At 1802, at least a second periodic structure of the metrology target is illuminated with a second radiation beam having a second different polarization. In an embodiment, the illumination of the first and second periodic structures occurs at a same time. In an embodiment, the second polarization is substantially orthogonal to the first polarization. In an embodiment, the first and second radiation beams are coherent with respect to each other.

In an embodiment, a beam splitter is used to split an incoming beam into the first radiation beam having the first polarization and the second radiation beam having the second polarization. In an embodiment, the beam splitter comprises a Wollaston or Nomarski prism. In an embodiment, the incoming beam has a polarization angle or a phase and/or amplitude of plane waves, between that of the first and second polarizations. In an embodiment, the beam splitter combines the radiation diffracted from the first periodic structure with the radiation diffracted from the second periodic structure. In an embodiment, the splitting plane of the beam splitter substantially coincides with a pupil plane, or a conjugate plane thereof, to produce a center of a spot of the first radiation beam on the target that is laterally displaced from a center of a spot of the second radiation beam on the target. In an embodiment, the splitting plane of the beam splitter substantially coincides with a field plane, or a conjugate plane thereof, to produce an angle of incidence of the first radiation beam on the target that is different an angle of incidence of the second radiation beam on the target.

In an embodiment, a center of a spot of the first radiation beam on the target is laterally displaced from a center of a spot of the second radiation beam on the target. In an embodiment, at least part of the second periodic structure does not overlie at least part of the first periodic structure and the center of the spot of the first radiation beam is incident on the at least part of the first periodic structure and the center of the spot of the second radiation beam is not incident on the at least part of the first periodic structure. In an embodiment, the spot of the first radiation beam on the target overlaps the spot of the second radiation beam on the target. In an embodiment, the spot of the first radiation beam and/or the spot of the second radiation beam is larger than the respective first periodic structure and/or second periodic structure.

In an embodiment, the angle of incidence of the first radiation beam on the target is different than the angle of incidence of the second radiation beam on the target. In an embodiment, at least part of the second periodic structure overlies at least part of the first periodic structure and the first and second radiation beams are incident on the at least part of the second periodic structure. In an embodiment, there is a periodic structure vector difference between the first and second periodic structures. In an embodiment, the periodic structure vector difference comprises a pitch of features of the first periodic structure being different from a pitch of features of the second periodic structure.

In an embodiment, the method further comprises changing the intensity ratio between the first and second radiation beams. In an embodiment, the method further comprises changing the phase between the first and second radiation beams. In an embodiment, the change in the intensity ratio and/or phase is performed on an incoming beam split into the first and second radiation beams.

In an embodiment, the first and second polarizations are about 45 degrees with respect to the direction of elongation of grating lines of the first and second periodic structures. In an embodiment, the first and second polarizations are linear polarizations.

At 1804, combining radiation diffracted from the first periodic structure is combined with radiation diffracted from the second periodic structure to cause interference. In an embodiment, the combined radiation is passed through a polarizer or retarder prior to detection.

At 1806, the combined radiation is detected using a detector. At 1808, a parameter of interest is determined from the detected combined radiation. In an embodiment, determining the parameter of interest comprises determining a parameter of interest for the target from the combined radiation and determining a parameter of interest specific to the first periodic structure and/or the second periodic structure from the combined radiation. In an embodiment, the parameter of interest comprises overlay. In an embodiment, the parameter of interest comprises diffraction efficiency and/or structural asymmetry, specific to the first periodic structure and/or the second periodic structure.

So, in an embodiment, there is provided a metrology apparatus comprising: an optical element configured to provide a first radiation beam having a first polarization and a second radiation beam having a second polarization onto a metrology target having a plurality of periodic structures; a detector configured to detect radiation from the first and second radiation beams diffracted by the periodic structures, wherein the diffracted radiation from the periodic structures is combined and interferes; and a control system configured to determine a parameter of interest from the detected combined diffracted radiation.

In an embodiment, the second polarization is substantially orthogonal to the first polarization. In an embodiment, the first and second radiation beams are coherent with respect to each other. In an embodiment, the first and second polarizations are about 45 degrees with respect to the direction of elongation of grating lines of the first and second periodic structures. In an embodiment, the first and second polarizations are linear polarizations. In an embodiment, the parameter of interest comprises overlay. In an embodiment, the parameter of interest comprises diffraction efficiency and/or structural asymmetry, specific to the first periodic structure and/or the second periodic structure.

In an embodiment, the optical element comprises a beam splitter configured to split an incoming beam into the first radiation beam having the first polarization and the second radiation beam having the second polarization. In an embodiment, the beam splitter comprises a Wollaston or Nomarski prism. In an embodiment, the incoming beam has a polarization angle or a phase and/or amplitude of plane waves, between that of the first and second polarizations. In an embodiment, the beam splitter combines the radiation diffracted from the first periodic structure with the radiation diffracted from the second periodic structure. In an embodiment, a center of a spot of the first radiation beam on the target is laterally displaced from a center of a spot of the second radiation beam on the target. In an embodiment, the splitting plane of the beam splitter substantially coincides with a pupil plane, or a conjugate plane thereof, to produce a center of a spot of the first radiation beam on the target that is laterally displaced from a center of a spot of the second radiation beam on the target. In an embodiment, at least part of the second periodic structure does not overlie at least part of the first periodic structure and the center of the spot of the first radiation beam is incident on the at least part of the first periodic structure and the center of the spot of the second radiation beam is not incident on the at least part of the first periodic structure. In an embodiment, the spot of the first radiation beam on the target overlaps the spot of the second radiation beam on the target. In an embodiment, the spot of the first radiation beam and/or the spot of the second radiation beam is larger than the respective first periodic structure and/or second periodic structure.

In an embodiment, the angle of incidence of the first radiation beam on the target is different than the angle of incidence of the second radiation beam on the target. In an embodiment, the splitting plane of the beam splitter substantially coincides with a field plane, or a conjugate plane thereof, to produce an angle of incidence of the first radiation beam on the target that is different an angle of incidence of the second radiation beam on the target. In an embodiment, at least part of the second periodic structure overlies at least part of the first periodic structure and the first and second radiation beams are incident on the at least part of the second periodic structure. In an embodiment, a pitch of features of the first periodic structure is different from a pitch of features of the second periodic structure.

In an embodiment, the apparatus further comprises a polarizer or retarder configured to change the intensity ratio between the first and second radiation beams. In an embodiment, the apparatus further comprises a retarder configured to change the phase between the first and second radiation beams.

In an embodiment, the apparatus further comprises a polarizer or retarder configured to process the combined radiation prior to detection.

In an embodiment, the control system configured to determine a parameter of interest from the detected combined is configured to determine a parameter of interest for the target from the combined radiation and determine a parameter of interest specific to the first periodic structure and/or the second periodic structure from the combined radiation.

Thus, in an embodiment, a target is illuminated with at least two coherent, orthogonally polarized beams. A spatial or angular separation of the at least two illumination beams is provided. Radiation diffracted by the target is combined (e.g., by an optical element or by the target itself) to interfere. The combined diffracted radiation is measured and a parameter of interest is determined from the measurement. A corresponding target design is provided (e.g., spatially separated upper and lower periodic structures or a periodic structure vector difference between upper and lower periodic structures). Active manipulation of target properties can be provided by using one or more polarizers and/or retarders in the optical path. For example, optimization of the intensity ratio and/or phase difference between the at least two illumination beams may be provided.

The apparatuses and/or metrology methods herein can enable, for example, better measurement accuracy, better measurement precision, better robustness of the measurements to process variation, a larger application range, a larger design freedom for the targets, and/or a larger freedom in wavelength choice.

As alluded to, proposed metrology target designs may be subject to testing and/or simulation in order to confirm their suitability and/or viability, both from a printability and a detectability standpoint. In a commercial environment, good overlay mark detectability may be considered to be a combination of low total measurement uncertainty as well as a short move-acquire-move time, as slow acquisition is detrimental to total throughput for the production line. Modern micro-diffraction-based-overlay targets (µDBO) may be on the order of 10-20 µm on a side.

Additionally, once metrology targets that meet the above criteria have been selected, there is a possibility that detectability will change with respect to typical process variations, such as film thickness variation, various etch biases, and/or geometry asymmetries induced by the etch and/or polish processes. Therefore, it may be useful to select a target that has low detectability variation and low variation in the measured parameter of interest (e.g., overlay, alignment, etc.) against various process variations. Likewise, the fingerprint (printing characteristics, including, for example, lens aberration) of the specific machine that is to be used to produce the microelectronic device to be imaged will, in general, affect the imaging and production of the metrology targets. It may therefore be useful to ensure that the metrology targets are resistant to fingerprint effects, as some patterns will be more or less affected by a particular lithographic fingerprint.

Accordingly, in an embodiment, there is provided a method to design a metrology target for use in the metrology methods and/or apparatuses described herein. In an embodiment, it is desirable to simulate various metrology target designs in order to confirm the suitability and/or viability of one or more of the proposed metrology target designs.

Figure 19:
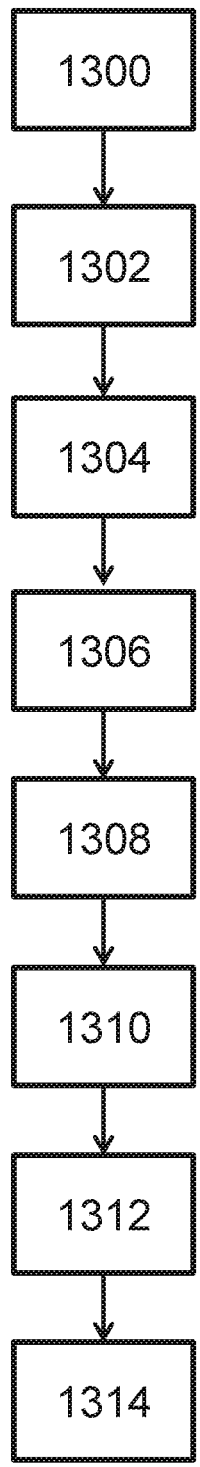
FIG. 19 schematically depicts an embodiment of a system to design a metrology target.

In a system for simulating a manufacturing process involving lithography and metrology targets, the major manufacturing system components and/or processes can be described by various functional modules, for example, as illustrated in FIG. 19. Referring to FIG. 19, the functional modules may include a design layout module 1300, which defines a metrology target (and/or microelectronic device) design pattern; a patterning device layout module 1302, which defines how the patterning device pattern is laid out in polygons based on the target design; a patterning device model module 1304, which models the physical properties of the pixilated and continuous-tone patterning device to be utilized during the simulation process; an optical model module 1306, which defines the performance of the optical components of the lithography system; a resist model module 1308, which defines the performance of the resist being utilized in the given process; a process model module 1310, which defines performance of the post-resist development processes (e.g., etch); and metrology module 1312, which defines the performance of a metrology system used with the metrology target (e.g., the metrology methods and/or apparatuses described herein) and thus the performance of the metrology target when used with the metrology system. The results of one or more of the simulation modules, for example, predicted contours and CDs, are provided in a result module 1314.

The properties of the illumination and projection optics are captured in the optical model module 1306 that includes, but is not limited to, NA-sigma (σ) settings as well as any particular illumination source shape, where σ (or sigma) is outer radial extent of the illuminator. The optical properties of the photo-resist layer coated on a substrate—i.e. refractive index, film thickness, propagation and polarization effects—may also be captured as part of the optical model module 1306, whereas the resist model module 1308 describes the effects of chemical processes which occur during resist exposure, post exposure bake (PEB) and development, in order to predict, for example, contours of resist features formed on the substrate. The patterning device model module 1304 captures how the target design features are laid out in the pattern of the patterning device and may include a representation of detailed physical properties of the patterning device, as described, for example, in U.S. Pat. No. 7,587,704. The objective of the simulation is to accurately predict, for example, edge placements and CDs, which can then be compared against the target design. The target design is generally defined as the pre-OPC patterning device layout, and will be provided in a standardized digital file format such as GDSII or OASIS.

In general, the connection between the optical and the resist model is a simulated aerial image intensity within the resist layer, which arises from the projection of radiation onto the substrate, refraction at the resist interface and multiple reflections in the resist film stack. The radiation intensity distribution (aerial image intensity) is turned into a latent "resist image" by absorption of photons, which is further modified by diffusion processes and various loading effects. Efficient simulation methods that are fast enough for full-chip applications approximate the realistic 3-dimensional intensity distribution in the resist stack by a 2-dimensional aerial (and resist) image.

Thus, the model formulation describes most, if not all, of the known physics and chemistry of the overall process, and each of the model parameters desirably corresponds to a distinct physical or chemical effect. The model formulation thus sets an upper bound on how well the model can be used to simulate the overall manufacturing process. However, sometimes the model parameters may be inaccurate from measurement and reading errors, and there may be other imperfections in the system. With precise calibration of the model parameters, extremely accurate simulations can be done.

In a manufacturing process, variations in various process parameters have significant impact on the design of a suitable target that can faithfully reflect a device design. Such process parameters include, but are not limited to, side-wall angle (determined by the etching or development process), refractive index (of a device layer or a resist layer), thickness (of a device layer or a resist layer), frequency of incident radiation, etch depth, floor tilt, extinction coefficient for the radiation source, coating asymmetry (for a resist layer or a device layer), variation in erosion during a chemical-mechanical polishing process, and the like.

Described herein is a computer-implemented method of defining a metrology target design for use in, e.g., a metrology system simulation or in a target manufacturing process simulation (e.g., including exposing the metrology target using a lithographic process, developing the metrology target, etching the target, etc.). In an embodiment, one or more design parameters (e.g., geometric dimensions) for the target can be specified and further discrete values or a range of values can be specified for the one or more design parameters. For example, one or more design parameters may specify that a periodic structure of an upper layer is laterally displaced relative to a periodic structure of a lower layer such that at least part of the periodic structure of the upper layer does not overlie at least part of the periodic structure of the lower layer. As another example, a design parameter may be a relationship of the lateral spacing of the upper and lower periodic structure based on lateral spacing of the first and second radiation beams discussed herein or the design parameter may be a relationship of a periodic structure vector difference (e.g., pitch difference between upper and lower periodic structures) based on the angle of incidence of the first and second radiation beams. Further, a user and/or the system may impose one or more constraints on one or more design parameters (e.g., a relationship between pitch and space width, a limit on pitch or space width, a relationship between feature (e.g., line) width (CD) and pitch (e.g., feature width is less than pitch), etc.) either in the same layer or between layers, based on, e.g., the patterning process for which the target is desired. For example, the constraint may be a relationship of lateral spacing of upper and lower periodic structures based on lateral spacing of the first and second radiation beams discussed herein or the constraint may be a relationship of a periodic structure vector difference (e.g., pitch difference between upper and lower periodic structures) based on the angle of incidence of the first and second radiation beams. In an embodiment, the one or more constraints may be on the one or more design parameters for which discrete values or a range has been specified, or on one or more other design parameters.

Figure 20:
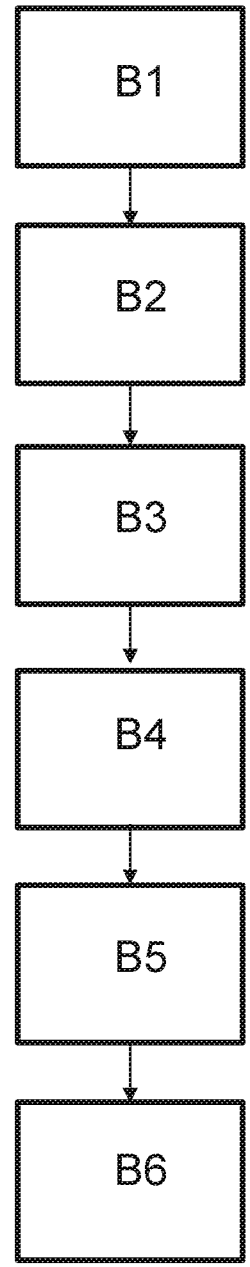
FIG. 20 depicts a flowchart illustrating an embodiment of a process of designing a metrology target.

FIG. 20 schematically depicts a computer-implemented method of defining a metrology target design in accordance with an embodiment. The method includes, at block B1, providing a range or a plurality of values for each of a plurality of design parameters (e.g., geometric dimensions) of a metrology target.

In an embodiment, a user of a metrology target design system may specify one or more of the design parameters (e.g., geometric dimensions) for the metrology target. The user may further specify the number of periodic structures 1000, 1010 of the metrology target. Further, in an embodiment, the user may specify (e.g., select) the discrete values or a range of values for each of one or more of the design parameters of the metrology target, one or more periodic structures thereof, and one or more periodic sub-structures of the periodic structures. For example, the user may select a range or a set of values for feature (e.g., line) width, space width, size of the metrology target, pitch, etc. for the metrology target. In an embodiment, where the metrology target comprises multiple periodic structures (gratings), or segmented periodic structures (gratings), the user may select or provide a range or set of values for other design parameters, e.g., shared pitch.

In an embodiment, the design parameters may include any one or more geometric dimensions selected from: pitch of a periodic structure of the target, periodic structure feature (e.g., line) width of the target, periodic structure space width of the target, one or more segmentation parameters of the features of the periodic structure (segmentation pitch/feature width/space width in X and/or Y direction depending on segmentation type). Further, the parameters may be specified for a single layer or a plurality of layers (e.g., two layers or two layers plus an intermediate shielding layer). For a plurality of layers, they may share pitch. For certain metrology targets, e.g. focus or alignment targets, other parameters may be used. Other design parameters may be physical limitations such as one or more selected from: a wavelength of radiation used in the metrology system for the target, polarization of radiation used in the metrology system, numerical aperture of the metrology system, target type, and/or a process parameter. In an embodiment, non-uniform and non-symmetric patterns, for example modulated overlay targets and focus targets, may be provided. Thus, the design parameters may be varied and not necessarily uniform in a particular direction.

At block B2, there is provided one or more constraints for one or more design parameters of the metrology target. Optionally, the user may define one or more constraints. A constraint may be a linear algebraic expression. In an embodiment, the constraint may be non-linear. Some constraints may be related to other constraints. For example, feature width, pitch and space width are related such that if any two of the three are known, the third may be fully determined.

In an embodiment, the user may specify a constraint on the area, a dimension, or both, of the metrology target. The user may specify a constraint on the number of periodic structures.

In an embodiment, a constraint may be a metrology parameter constraint. For example, in some metrology systems, the physics of the system may place a constraint. For example, a wavelength of radiation used in the system may constrain the pitch of the target design, e.g., a lower limit. In an embodiment, there is a (upper/lower) limit on pitch as function of wavelength, the type of target and/or the aperture of the metrology system. Physical limitations that can be used as constraints include one or more selected from: a wavelength of radiation used in the metrology system, polarization of radiation used in the metrology system, numerical aperture of the metrology system, and/or target type. In an embodiment, the constraint may be a process parameter constraint (e.g., a constraint dependent on etch type, development type, resist type, etc.).

Depending on the particular process being used, in an embodiment, one or more constraints may be related to a constraint between a design parameter (e.g., geometric dimension) of one layer and a design parameter (e.g., geometric dimension) of another layer.

At block B3, by a processor, the method solves for and/or selects by sampling within the range or the plurality of values for the design parameters, a plurality of metrology target designs having one or more design parameters meeting the one or more constraints. For example, in an embodiment involving solving, one or more potential metrology targets design may be solved for. That is, one or more potential metrology designs may be derived by solving for permitted values using, e.g., one or more equality constraints to solve for specific values. For example, in an embodiment involving sampling, a convex polytope may be defined by the various design parameters and constraints. The volume of the convex polytope may be sampled according to one or more rules to provide sample metrology target designs that meet all the constraints. One or more sampling rules may be applied to sample metrology target designs.

It is to be noted, however, that not all metrology target designs thus discovered are equally representative of process variations. As such, in an embodiment, the metrology target designs discovered using a method described herein may be further simulated, at block B4, to determine, for example, the viability and/or suitability of one or more of the metrology target designs. The simulated metrology target designs may then be evaluated at block B5 to identify which one or more metrology target designs are best or more representative of process variation by, for example, ranking them based on a key performance index or a robustness criteria. At block B6, a particular metrology design may be selected and used, e.g., for measurement.

Figure 21:
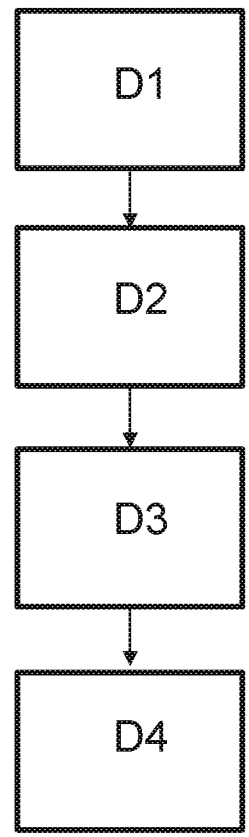
FIG. 21 depicts a flowchart illustrating an embodiment of a process in which the metrology target is used to monitor performance, and as a basis for controlling metrology, design and/or production processes.

FIG. 21 shows a flowchart illustrating a process in which the metrology target is used to monitor performance, and as a basis for controlling metrology, design and/or production processes. In step D1, substrates are processed to produce product features and one or more metrology targets as described herein. At step D2, patterning process parameter (e.g., overlay) values are measured and calculated using, e.g., a method and/or apparatus as described herein. At step D3, the measured patterning process parameter (e.g., overlay) value may be used (together with other information as may be available), to update a metrology recipe. The updated metrology recipe is used for re-measurement of the patterning process parameter, and/or for measurement of the patterning process parameter on a subsequently processed substrate. In this way, the calculated patterning process parameter is improved in accuracy. The updating process can be automated if desired. In step D4, the patterning process parameter value is used to update a recipe that controls the patterning step and/or other process step in the device manufacturing process for re-work and/or for processing of further substrates. Again this updating can be automated if desired.

While the embodiments of the metrology target described herein have mostly been described in the terms of overlay measurement, the embodiments of the metrology target described herein may be used to measure one or more additional or alternative patterning process parameters. For example, the metrology target may be used to measure exposure dose variation, measure exposure focus/defocus, etc. In an embodiment, a same metrology target may be used to measure a plurality of different parameters. For example, the metrology target may be arranged to measure overlay and measure one or more other parameters such as critical dimension, focus, dose, etc. As an example, one or more of the periodic structures may be designed to measure overlay (e.g., have their associated periodic structures in different layers) and one or more other periodic structures may be designed to measure critical dimension, and/or focus, and/or dose, etc. In an embodiment, a particular combination of periodic structures may be designed to measure two or more parameters, e.g., overlay and one or more other parameters such as critical dimension, focus, dose, etc. As discussed herein, a plurality of periodic structures can be measured with a plurality of radiation beams and the combined diffracted radiation from the plurality of periodic structures can be used to measure a parameter from the combination of the plurality of periodic structures (e.g., overlay) and a parameter specific to one or more of the periodic structures (e.g., structural asymmetry, diffraction efficiency, etc.).

While the target structures described above are metrology targets specifically designed and formed for the purposes of measurement, in other embodiments, properties may be measured on targets which are functional parts of devices formed on the substrate. Many devices have regular, grating-like structures. The terms 'target grating' and 'target periodic structure' as used herein do not require that the structure has been provided specifically for the measurement being performed. Further, pitch P of the metrology target is close to the resolution limit of the optical system of the scatterometer, but may be much larger than the dimension of typical product features made by patterning process in the target portions C. In practice the features and/or spaces of the overlay periodic structures may be made to include smaller structures similar in dimension to the product features.

Further, the Figures are merely exemplary of the periodic structures of the targets. For example, some Figures may show just a few periodic features of a periodic structure when in practice, the periodic structure may have many more periodic features.

In certain embodiment, the periodic structures of the metrology target may be rotationally symmetric. That is there may be two or more periodic structures (e.g., three or more, four or more, etc.) of the metrology target, wherein the periodic structures are configured to share a common center of symmetry and each periodic structure is invariant to 180 degree or more rotation about the common center of symmetry. Further, each periodic structure may include two or more periodic sub-structures (e.g., three or more, four or more, etc.), wherein each of the periodic sub-structures has an individual center of symmetry and each periodic sub-structure is invariant to 180 degree or more rotation about the individual center of symmetry.

But, in an embodiment, the periodic structures of a metrology target may be rotationally asymmetric. This may be accomplished in any of a number of ways. For example, a periodic structure of three of more periodic structures may be shifted (located) away from a common center of symmetry of the other periodic structures. As another example, one or more of the features of one or more of the periodic structures may be slightly shortened, lengthened or shifted relative to one or more of the features of one or more other periodic structures. As another example, one or more dummy structures may be inserted between periodic structures to disrupt any symmetry. In an embodiment, the one or more dummy structures are rotationally asymmetric. The shift, shortening or lengthening may be below the measurable range of the measurement apparatus. In an embodiment, the shift, shortening or lengthening is in the 1 nm range or less. Such a change will have small to negligible effect on measurement readings. Similarly, the dummy structures may have feature size or pitch below the effective measurement range of the measurement apparatus.

While embodiments have been described in terms of dark field metrology, the embodiments herein may be appropriately applied to angle-resolved and/or image metrology.

The term "structure" is used herein without limitation to any particular form of structure such as a simple grating line. Indeed, coarse structural features, such as the lines and spaces of a grating, can be formed by collections of finer sub-structures.

In association with the physical periodic structures of the targets as realized on substrates and patterning devices, an embodiment may include a computer program containing one or more sequences of machine-readable instructions describing a method of designing a target for a substrate, a method of producing a target on a substrate, a method of measuring a target on a substrate and/or a method of analyzing a measurement to obtain information about a patterning process. An embodiment may comprise computer code containing one or more sequences of machine-readable instructions or data describing the target. This computer program or code may be executed for example within unit PU in the apparatus of FIG. 3 and/or the control unit LACU of FIG. 2. There may also be provided a data storage medium (e.g., semiconductor memory, magnetic or optical disk, etc.) having such a computer program or code stored therein. Where an existing metrology apparatus, for example of the type shown in FIG. 3, is already in production and/or in use, an embodiment of the invention can be implemented by the provision of an updated computer program product for causing a processor to perform one or more of the method described herein. The computer program or code may optionally be arranged to control the optical system, substrate support and the like to perform a method of measuring a parameter of the patterning process on a suitable plurality of targets. The computer program or code can update the lithographic and/or metrology recipe for measurement of further substrates. The computer program or code may be arranged to control (directly or indirectly) the lithographic apparatus for the patterning and processing of further substrates. In an embodiment, there is provided a non-transitory computer program product comprising machine-readable instructions or data defining a measurement target as described herein. In an embodiment, there is provided a substrate comprising a measurement target as described herein. In an embodiment, there is provided a patterning device configured to at least in part form a measurement target as described herein.

Further embodiments according to the invention are provided in below numbered clauses:

1. A method, comprising:
   illuminating at least a first periodic structure of a metrology target with a first radiation beam having a first polarization;
   illuminating at least a second periodic structure of the metrology target with a second radiation beam having a second different polarization;
   combining radiation diffracted from the first periodic structure with radiation diffracted from the second periodic structure to cause interference;
   detecting the combined radiation using a detector; and
   determining a parameter of interest from the detected combined radiation.
2. The method of clause 1, wherein the second polarization is substantially orthogonal to the first polarization.
3. The method of clause 1 or clause 2, wherein the first and second radiation beams are coherent with respect to each other.
4. The method of any of clauses 1-3, further comprising using a beam splitter to split an incoming beam into the first radiation beam having the first polarization and the second radiation beam having the second polarization.
5. The method of clause 4, wherein the beam splitter comprises a Wollaston or Nomarski prism.
6. The method of clause 4 or clause 5, wherein the incoming beam has a polarization angle or a phase and/or amplitude of plane waves, between that of the first and second polarizations.
7. The method of any of clauses 4-6, wherein the beam splitter combines the radiation diffracted from the first periodic structure with the radiation diffracted from the second periodic structure.
8. The method of any of clauses 4-7, wherein the splitting plane of the beam splitter substantially coincides with a pupil plane, or a conjugate plane thereof, to produce a center of a spot of the first radiation beam on the target that is laterally displaced from a center of a spot of the second radiation beam on the target.
9. The method of any of clauses 4-7, wherein the splitting plane of the beam splitter substantially coincides with a field plane, or a conjugate plane thereof, to produce an angle of incidence of the first radiation beam on the target that is different an angle of incidence of the second radiation beam on the target.
10. The method of any of clauses 1-8, wherein a center of a spot of the first radiation beam on the target is laterally displaced from a center of a spot of the second radiation beam on the target.
11. The method of clause 10, wherein at least part of the second periodic structure does not overlie at least part of the first periodic structure and the center of the spot of the first radiation beam is incident on the at least part of the first periodic structure and the center of the spot of the second radiation beam is not incident on the at least part of the first periodic structure.
12. The method of clause 10 or clause 11, wherein the spot of the first radiation beam on the target overlaps the spot of the second radiation beam on the target.
13. The method of any of clauses 10-12, wherein the spot of the first radiation beam and/or the spot of the second radiation beam is larger than the respective first periodic structure and/or second periodic structure.
14. The method of any of clauses 1-7 or 9, wherein the angle of incidence of the first radiation beam on the target is different than the angle of incidence of the second radiation beam on the target.
15. The method of clause 14, wherein at least part of the second periodic structure overlies at least part of the first periodic structure and the first and second radiation beams are incident on the at least part of the second periodic structure.
16. The method of clause 14 or clause 15, wherein a pitch of features of the first periodic structure is different from a pitch of features of the second periodic structure.
17. The method of any of clauses 1-16, further comprising changing the intensity ratio between the first and second radiation beams.
18. The method of any of clauses 1-17, further comprising changing the phase between the first and second radiation beams.

19. The method of any of clauses 1-18, wherein the first and second polarizations are about 45 degrees with respect to the direction of elongation of grating lines of the first and second periodic structures.
20. The method of any of clauses 1-19, further comprising passing the combined radiation through a polarizer or retarder prior to detection.
21. The method of any of clauses 1-20, wherein the first and second polarizations are linear polarizations.
22. The method of any of clauses 1-21, wherein comprising determining the parameter of interest comprises determining a parameter of interest for the target from the combined radiation and determining a parameter of interest specific to the first periodic structure and/or the second periodic structure from the combined radiation.
23. The method of any of clauses 1-22, wherein the parameter of interest comprises overlay.
24. The method of any of clauses 1-22, wherein the parameter of interest comprises diffraction efficiency and/or structural asymmetry, specific to the first periodic structure and/or the second periodic structure.
25. The method of any of clauses 1-24, further comprising optimizing the first and/or second polarizations.
26. The method of clause 25, wherein the optimizing is performed based on observed properties of the metrology target.
27. The method of clause 25 or clause 26, wherein the optimizing comprises optimizing a plurality of metrology target parameters.
28. The method of clause 27, wherein the metrology target parameters comprise one or more parameters selected from: stack sensitivity, diffraction efficiency, sensitivity to structural asymmetry of a lower periodic structure, and/or matching to an external reference.
29. A metrology apparatus comprising:
    an optical element configured to provide a first radiation beam having a first polarization and a second radiation beam having a second polarization onto a metrology target having a plurality of periodic structures;
    a detector configured to detect radiation from the first and second radiation beams diffracted by the periodic structures, wherein the diffracted radiation from the periodic structures is combined and interferes; and
    a control system configured to determine a parameter of interest from the detected combined diffracted radiation.
30. The apparatus of clause 29, wherein the second polarization is substantially orthogonal to the first polarization.
31. The apparatus of clause 29 or clause 30, wherein the first and second radiation beams are coherent with respect to each other.
32. The apparatus of any of clauses 29-31, wherein the optical element comprises a beam splitter configured to split an incoming beam into the first radiation beam having the first polarization and the second radiation beam having the second polarization.
33. The apparatus of clause 32, wherein the beam splitter comprises a Wollaston or Nomarski prism.
34. The apparatus of clause 32 or clause 33, wherein the incoming beam has a polarization angle or a phase and/or amplitude of plane waves, between that of the first and second polarizations.
35. The apparatus of any of clauses 32-34, wherein the beam splitter combines the radiation diffracted from the first periodic structure with the radiation diffracted from the second periodic structure.
36. The apparatus of any of clauses 32-35, wherein the splitting plane of the beam splitter substantially coincides with a pupil plane, or a conjugate plane thereof, to produce a center of a spot of the first radiation beam on the target that is laterally displaced from a center of a spot of the second radiation beam on the target.
37. The apparatus any of clauses 32-35, wherein the splitting plane of the beam splitter substantially coincides with a field plane, or a conjugate plane thereof, to produce an angle of incidence of the first radiation beam on the target that is different an angle of incidence of the second radiation beam on the target.
38. The apparatus any of clauses 29-36, wherein a center of a spot of the first radiation beam on the target is laterally displaced from a center of a spot of the second radiation beam on the target.
39. The apparatus of clause 38, wherein at least part of the second periodic structure does not overlie at least part of the first periodic structure and the center of the spot of the first radiation beam is incident on the at least part of the first periodic structure and the center of the spot of the second radiation beam is not incident on the at least part of the first periodic structure.
40. The apparatus of clause 39 or clause 39, wherein the spot of the first radiation beam on the target overlaps the spot of the second radiation beam on the target.
41. The apparatus of any of clauses 38-40, wherein the spot of the first radiation beam and/or the spot of the second radiation beam is larger than the respective first periodic structure and/or second periodic structure.
42. The apparatus of any of clauses 29-35 or 37, wherein the angle of incidence of the first radiation beam on the target is different than the angle of incidence of the second radiation beam on the target.
43. The apparatus of clause 42, wherein at least part of the second periodic structure overlies at least part of the first periodic structure and the first and second radiation beams are incident on the at least part of the second periodic structure.
44. The apparatus of clause 42 or clause 43, wherein a pitch of features of the first periodic structure is different from a pitch of features of the second periodic structure.
45. The apparatus of any of clauses 29-44, further comprising a polarizer or retarder configured to change the intensity ratio between the first and second radiation beams.
46. The apparatus of any of clauses 29-45, further comprising a retarder configured to change the phase between the first and second radiation beams.
47. The apparatus of any of clauses 29-46, wherein the first and second polarizations are about 45 degrees with respect to the direction of elongation of grating lines of the first and second periodic structures.
48. The apparatus of any of clauses 29-47, further comprising a polarizer or retarder configured to process the combined radiation prior to detection.
49. The apparatus of any of clauses 29-48, wherein the first and second polarizations are linear polarizations.
50. The apparatus of any of clauses 29-49, wherein the control system configured to determine a parameter of interest from the detected combined is configured to determine a parameter of interest for the target from the combined radiation and determine a parameter of interest specific to the first periodic structure and/or the second periodic structure from the combined radiation.
51. The apparatus of any of clauses 29-50, wherein the parameter of interest comprises overlay.
52. The apparatus of any of clauses 29-51, wherein the parameter of interest comprises diffraction efficiency and/ or structural asymmetry, specific to the first periodic structure and/or the second periodic structure.

53. The apparatus any of clauses 29-52, wherein the control system is further configured to optimize the first and/or second polarizations.

54. A method of manufacturing devices wherein a device pattern is applied to a series of substrates using a patterning process, the method including inspecting at least a diffraction measurement target formed as part of or beside the device pattern on at least one of the substrates using the method of any of clauses 1-28, and controlling the patterning process for later substrates in accordance with the result of the method.

55. A non-transitory computer program product comprising machine-readable instructions for causing a processor to cause performance of the method of any of clauses 1-28.

56. A system comprising:
an inspection apparatus configured to provide a beam on a diffraction measurement target on a substrate and to detect radiation diffracted by the target to determine a parameter of a patterning process; and
the non-transitory computer program product of clause 55.

57. The system of clause 56, further comprising a lithographic apparatus comprising a support structure configured to hold a patterning device to modulate a radiation beam and a projection optical system arranged to project the modulated onto a radiation-sensitive substrate.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate. The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

The term "optimizing" and "optimization" as used herein mean adjusting an apparatus or process, e.g., a lithographic apparatus or an optical lithography process step, such that patterning and/or device fabrication results and/or processes (e.g., of lithography) have one or more desirable characteristics, such as higher accuracy of projection of a design layout on a substrate, larger process window, etc.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments reveals the general nature of embodiments of the invention such that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. A method, comprising:
illuminating at least a first periodic structure of a metrology target with radiation having a first polarization;
illuminating at least a second periodic structure of the metrology target with radiation having a second different polarization, wherein the radiation having the first polarization and the radiation having the second polarization form a single beam spot on the metrology target or form respective beam spots that overlap on the metrology target;
combining radiation diffracted from the first periodic structure with radiation diffracted from the second periodic structure to cause interference;
detecting the combined radiation using a detector; and
determining a parameter of interest from the detected combined radiation.

2. The method of claim 1, wherein the second polarization is substantially orthogonal to the first polarization.

3. The method of claim 1, wherein the radiation having the first polarization and the radiation having the second polarization form respective beam spots that overlap on the metrology target and wherein respective radiation beams associated with the respective beam spots are coherent with respect to each other.

4. The method of claim 1, wherein the radiation having the first polarization and the radiation having the second polarization form respective beam spots that overlap on the metrology target and wherein a central portion of a first beam spot of the beam spots on the metrology target is laterally displaced from a central portion of a second beam spot of the beam spots on the metrology target.

5. The method of claim 4, wherein at least part of the second periodic structure does not overlie at least part of the first periodic structure and the central portion of the first beam spot is incident on the at least part of the first periodic structure and the central portion of the second beam spot is not incident on the at least part of the first periodic structure.

6. The method of claim 1, further comprising determining the parameter of interest from a value of an intensity difference or ratio determined using the detected combined radiation.

7. The method of claim 1, further comprising changing an intensity ratio between the radiation having the first polarization and the radiation having the second polarization.

8. The method of claim 1, further comprising changing a phase between the radiation having the first polarization and the radiation having the second polarization.

9. The method of claim 1, wherein determining the parameter of interest comprises determining a parameter of interest for the target from the combined radiation and determining a parameter of interest specific to the first periodic structure and/or the second periodic structure from the combined radiation.

10. A metrology apparatus comprising:
an optical system configured to provide radiation having a first polarization onto at least a first periodic structure of a metrology target and radiation having a second polarization onto at least a second periodic structure of the metrology target, wherein the optical system is configured to provide the radiation having the first polarization and the radiation having the second polarization as a single beam spot on the metrology target or as respective beam spots that overlap on the metrology target;
a detector configured to detect radiation from the radiation having the first and second polarizations diffracted by the respective first and second periodic structures, wherein the diffracted radiation from the first and second periodic structures is combined and interferes; and
a control system configured to determine a parameter of interest from the detected combined diffracted radiation.

11. The apparatus of claim 10, wherein the second polarization is substantially orthogonal to the first polarization.

12. The apparatus of claim 10, wherein the radiation having the first polarization and the radiation having the second polarization form respective beam spots that overlap on the metrology target and wherein respective radiation beams associated with the respective beam spots are coherent with respect to each other.

13. The apparatus of claim 10, wherein the radiation having the first polarization and the radiation having the second polarization form respective beam spots that overlap on the metrology target and wherein the optical system is configured to provide a central portion of a first beam spot of the beam spots on the metrology target at a laterally displaced position from a central portion of a second beam spot of the beam spots on the metrology target.

14. The apparatus of claim 10, further comprising a polarizer or retarder configured to change an intensity ratio between the radiation having the first polarization and the radiation having the second polarization.

15. The apparatus of claim 10, further comprising a retarder configured to change a phase between the radiation having the first polarization and the radiation having the second polarization.

16. The apparatus of claim 10, wherein the control system configured to determine a parameter of interest from the detected combined radiation is configured to determine a parameter of interest for the target from the combined radiation and determine a parameter of interest specific to the first periodic structure and/or the second periodic structure from the combined radiation.

17. The apparatus of claim 10, wherein the control system is configured to determine the parameter of interest from a value of an intensity difference or ratio determined using the detected combined radiation.

18. A non-transitory computer program product comprising machine-readable instructions that, when executed by a computer system, are configured to cause the computer system to at least:
enable illumination of at least a first periodic structure of a metrology target with radiation having a first polarization;
enable illumination of at least a second periodic structure of the metrology target with radiation having a second different polarization, wherein radiation diffracted from the first periodic structure combines with radiation diffracted from the second periodic structure to cause interference;
enable detection of the combined radiation using a detector; and
determine a parameter of interest from a value of an intensity difference or ratio determined using the detected combined radiation.

19. The computer program product of claim 18, wherein the radiation having the first polarization and the radiation having the second polarization are formed as a single beam spot on the metrology target or as respective beam spots that overlap on the metrology target.

20. A system comprising:
an inspection apparatus configured to provide a beam on a diffraction metrology target on a substrate and to detect radiation diffracted by the metrology target to determine a parameter of interest of a patterning process; and
the non-transitory computer program product of claim 18.

* * * * *